US00RE47034E

(19) United States
(12) Reissued Patent
Sun et al.

(10) Patent Number: US RE47,034 E
(45) Date of Reissued Patent: Sep. 11, 2018

(54) TOPICAL FORMULATION FOR ADMINISTERING A COMPOUND

(71) Applicant: Rigel Pharmaceuticals, Inc., South San Francisco, CA (US)

(72) Inventors: Thomas Sun, Palo Alto, CA (US); Matt Duan, Foster City, CA (US)

(73) Assignee: Rigel Pharmaceuticals, Inc., South San Francisco, CA (US)

(21) Appl. No.: 15/604,502

(22) Filed: May 24, 2017

Related U.S. Patent Documents

Reissue of:
(64) Patent No.: 9,040,061
Issued: May 26, 2015
Appl. No.: 13/707,264
Filed: Dec. 6, 2012

U.S. Applications:
(60) Provisional application No. 61/609,129, filed on Mar. 9, 2012, provisional application No. 61/568,443, filed on Dec. 8, 2011.

(51) Int. Cl.
*A61K 9/00* (2006.01)
*A61K 31/635* (2006.01)
*A61K 47/10* (2017.01)
*A61K 31/505* (2006.01)

(52) U.S. Cl.
CPC ..... *A61K 31/635* (2013.01); *A61K 9/0014* (2013.01); *A61K 31/505* (2013.01); *A61K 47/10* (2013.01)

(58) Field of Classification Search
CPC ..... A61K 31/635
USPC ..... 424/400
See application file for complete search history.

(56) References Cited

U.S. PATENT DOCUMENTS 4,082,881 A * 4/1978 Chen et al. ..... 514/39
6,482,397 B1 * 11/2002 Scott et al. ..... 424/59
2006/0039931 A1 * 2/2006 Scheiwe et al. ..... 424/400
2007/0203161 A1 * 8/2007 Argade et al. ..... C07D 239/48 514/275
2011/0028503 A1 * 2/2011 Taylor ..... A61K 9/0048 514/275
2012/0232106 A1 * 9/2012 Magilavy ..... A61K 31/506 514/275

FOREIGN PATENT DOCUMENTS

WO WO 2008007182 A2 * 1/2008

OTHER PUBLICATIONS

Torsten Henning ("Henning", 2002, Clarian GMBH "Polyethylene glycols (PEGs) and the pharmaceutical industry").*
Nassar et al. Pharm. Dev and Tech., 2004, 9(2), 189-195.*
Macrogol (Ultra-pure Macrogol, 200, 300 and 400, http://www.nof-solubilizer.com/peg-200_300and400.html).*
Lutrol® E Liquid grades, Technical Information, Dec. 2010, http://www.innovate-excipients.basf.com/Statements/Technical %20Informations/EN/Pharma%20Solutions/03_030734e_Lutrol %20E%20-%20Liquid%20Grades.pdf.*

* cited by examiner

*Primary Examiner* — Timothy J Kugel
(74) *Attorney, Agent, or Firm* — Travis Young; Klarquist Sparkman, LLP

(57) ABSTRACT

Embodiments of topical formulations for administering compound I or a pharmaceutically acceptable salt or solvate thereof are disclosed. Embodiments of methods for using the topical formulations in the treatment of dermatological disorders such as cutaneous collagen vascular diseases, e.g., cutaneous lupus, also are disclosed.

Compound I

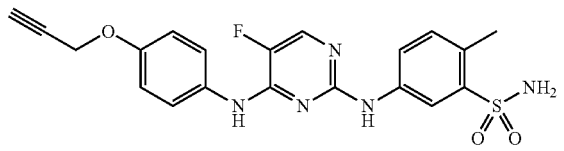

32 Claims, No Drawings

TOPICAL FORMULATION FOR ADMINISTERING A COMPOUND

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

The present application claims the benefit of the earlier filing dates of U.S. provisional application No. 61/568,443, filed Dec. 8, 2011, and U.S. provisional application No. 61/609,129, filed on Mar. 9, 2012, both of which are incorporated herein by reference in their entirety.

FIELD

The present disclosure relates to a compound, topical formulations thereof, and methods of using the compound and/or topical formulations thereof in the treatment of dermatological disorders, such as a cutaneous collagen vascular disease, for example a cutaneous lupus disorder.

BACKGROUND

JAK kinases (JAnus Kinases) are a family of cytoplasmic protein tyrosine kinases including JAK1, JAK2, JAK3 and TYK2. Each of the JAK kinases is selective for the receptors of certain cytokines, though multiple JAK kinases may be affected by particular cytokine or signaling pathways. Studies suggest that JAK3 associates with the common gamma (c) chain of the various cytokine receptors. JAK3 in particular selectively binds to receptors and is part of the cytokine signaling pathway for IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-$\alpha$. Upon binding of certain cytokines to their receptors (for example, IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes. JAK/STAT signaling has been implicated in the mediation of many abnormal immune responses such as allergies, asthma, autoimmune diseases such as transplant (allograft) rejection, rheumatoid arthritis, amyotrophic lateral sclerosis, systemic lupus erythematosus and multiple sclerosis, ocular disorders and diseases, as well as in solid and hematologic malignancies such as leukemia and lymphomas.

Connective tissue disorders are a group of diseases that affect a broad variety of organs, and are sometimes referred to as collagen vascular diseases. This class of diseases includes many distinct inflammatory disorders, such as vasculitis, discoid lupus erythematosus (DLE), systemic lupus erythematosus (SLE), progressive systemic sclerosis, polymyositis/dermatomyositis, polymyalgia rheumatic, polyarteritis nodosa, and Wegener's granulomatosis. These are distinct diseases that have been clinically distinguished from each other for purposes of diagnosis, prognosis, and treatment. Lupus erythematosus is a generic category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain anti-nuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Conventional DLE treatments have included topical corticosteroid ointments or creams, such as triamcinolone acetonide, fluocinolone, flurandrenolide, betamethasone valerate, or betamethasone dipropionate. Resistant plaques can be injected with an intradermal corticosteroid. However, prolonged use of corticosteroids themselves can lead to serious side effects, such as skin atrophy, striae, easy bruising and tearing of the skin, dermatitis, telangiectasia, and increased susceptibility to infection. Other potential DLE treatments include calcineurin inhibitors such as pimecrolimus cream or tacrolimus ointment. Particularly resistant cases can be treated with systemic antimalarial drugs, such as hydroxychloroquine (PLAQUENIL). However, this drug carries the risk of significant retinal toxicity with bull's eye retinopathy. Even after cessation of the drug, visual loss may continue and no medical therapy has been found to reverse the retinal damage.

DLE is a disfiguring disease for which current therapies have proven unsatisfactory. Treatments are also needed for the other cutaneous forms of lupus, such as the acute and sub-acute forms.

SUMMARY

Certain disclosed embodiments concern a pharmaceutical formulation, typically formulated for topical administration, comprising a therapeutically effective amount of a Compound I (below)

Compound I

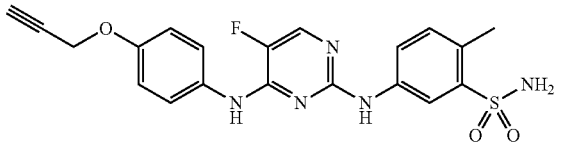

or a pharmaceutically acceptable salt thereof, such as a hydrochloride salt or a besylate salt. Particular embodiments of the formulation comprise a therapeutically effective amount of the compound, a topical base, an antioxidant, and an emollient. A person of ordinary skill in the art will appreciate that a therapeutically effective amount of the compound may vary, but typically the therapeutically effective amount is from 0.1% to 10% (w/w).

The topical base may comprise polyethylene glycol having a selected molecular weight. Particular embodiments comprise a polyethylene glycol having a molecular weight of from 3000 to 8000 daltons as a topical base.

In certain embodiments, the formulation is an ointment, and may further comprise a water-miscible solvent, such as a polyalkylene glycol having an average molecular weight of from 200 daltons to 600 daltons. In certain embodiments the water-miscible solvent comprises PEG-400, and even more particularly PEG-400 substantially free of impurities. In certain embodiments, the PEG-400 comprises less than 65 ppm formaldehyde, less than 10 ppm formaldehyde, or 1 ppm or less formaldehyde. In one aspect, the water-miscible solvent includes glycofurol, which can be used in place of or in combination with a low molecular weight polyalkylene glycol, particularly a polyethylene glycol, such as PEG-400.

The pharmaceutical formulation also can include a penetration enhancer, such as dimethyl isosorbide, propylene glycol, and combinations thereof; an emollient, such as water; a surfactant, such as sorbitan monostearate, a polyethylene glycol monostearate, D-α-tocopheryl polyethylene glycol 1000 succinate, a composition comprising glycol stearate/PEG32 stearate/PEG6 stearate, and combinations of surfactants; an antioxidant, such as butylated hydroxyanisole, butylated hydroxytoluene, ascorbic acid, a tocopherol, and combinations thereof, with particular embodiments comprising butylated hydroxytoluene as the antioxidant; and a colorant, such as 0.05% to 0.25% (w/w) caramel colorant.

For particular embodiments the therapeutically effective amount is from 0.1% to 10% (w/w), and the pharmaceutical formulation further comprises: from 15% to 40% (w/w) of a topical base, such as a polyalkylene glycol with an average molecular weight of from 4000 to 5000 daltons; from 25% to 50% (w/w) of a water-miscible solvent, such as a polyalkylene glycol with an average molecular weight of from 300 to 500 daltons; from 10% to 20% (w/w) of a penetration enhancer, such as dimethyl isosorbide; from 3% to 15% (w/w) of an emollient, such as water; from 3% to 9% (w/w) of a surfactant, such as polyethylene glycol monostearate; and from 0.5% to 1.5% (w/w) butylated hydroxytoluene as an antioxidant. The pharmaceutical formulation may further comprise from 0.05% to 0.25% of a colorant, such as a caramel colorant.

For particular embodiments the therapeutically effective amount is from 0.1% to 10% (w/w), and the pharmaceutical formulation further comprises: from 15% to 25% (w/w) of a topical base, such as a polyalkylene glycol with an average molecular weight of from 4000 to 5000 daltons; from 40% to 50% (w/w) of a water-miscible solvent, such as a polyalkylene glycol with an average molecular weight of from 300 to 500 daltons; from 10% to 20% (w/w) of a penetration enhancer, such as dimethyl isosorbide; from 5% to 15% (w/w) of an emollient, such as water; from 3% to 7% (w/w) of a surfactant, such as polyethylene glycol monostearate; and from 0.5% to 1.5% (w/w) butylated hydroxytoluene as an antioxidant. The pharmaceutical formulation may further comprise from 0.05% to 0.25% of a colorant, such as a caramel colorant.

In other disclosed embodiments, the pharmaceutical formulation comprises from 0.2% to 6% (w/w) of compound I or a pharmaceutically acceptable salt thereof; from 30% to 40% or from 25% to 40% (w/w) polyethylene glycol with an average molecular weight of from 4000 to 5000 daltons; from 30% to 40% or from 30% to 45% (w/w) polyethylene glycol with an average molecular weight of from 300 to 500 daltons; 15% (w/w) dimethyl isosorbide; from 3% to 5% (w/w) water; 5% (w/w) polyethylene glycol monostearate; 1% (w/w) butylated hydroxytoluene, and 0.05% caramel colorant.

Another embodiment of the pharmaceutical formulation comprises from 0.2% to 6% (w/w) of compound I or a pharmaceutically acceptable salt thereof; 20% (w/w) polyethylene glycol with an average molecular weight of from 4000 to 5000 daltons; from 43% to 48.8% (w/w) polyethylene glycol with an average molecular weight of from 300 to 500 daltons; 15% (w/w) dimethyl isosorbide; 10% (w/w) water; 5% (w/w) polyethylene glycol monostearate; and 1% (w/w) butylated hydroxytoluene.

Yet another embodiment of the pharmaceutical comprises 1% (w/w) compound I, from 25% to 40% (w/w) polyethylene glycol with an average molecular weight of 4500 daltons, and from 30% to 45% (w/w) polyethylene glycol with an average molecular weight of 400 daltons.

Yet another embodiment of the pharmaceutical comprises 3% (w/w) compound I, 32% (w/w) polyethylene glycol with an average molecular weight of 4500 daltons, and from 38% to 42% (w/w) polyethylene glycol with an average molecular weight of 400 daltons.

Yet another embodiment of the pharmaceutical comprises 6% (w/w) compound I, 35% (w/w) polyethylene glycol with an average molecular weight of 4500 daltons, and from 33% to 35% (w/w) polyethylene glycol with an average molecular weight of 400 daltons.

Yet another embodiment of the pharmaceutical formulation comprises 1% (w/w) compound I; 20% (w/w) polyethylene glycol with an average molecular weight of 4500 daltons; and 48% (w/w) polyethylene glycol with an average molecular weight of 400 daltons.

Yet another embodiment of the pharmaceutical formulation comprise 3% (w/w) compound I; 20% (w/w) polyethylene glycol with an average molecular weight of 500 daltons; and 46% (w/w) polyethylene glycol with an average molecular weight of 400 daltons.

Yet another embodiment of the pharmaceutical formulation comprises 6% (w/w) compound I; 20% (w/w) polyethylene glycol with an average molecular weight of 4500 daltons; and 43% (w/w) polyethylene glycol with an average molecular weight of 400 daltons.

Yet another embodiment of the pharmaceutical formulation comprises 3% (w/w) of compound I or a pharmaceutically acceptable salt thereof; 32% (w/w) polyethylene glycol 4500 daltons; 39.95% (w/w) polyethylene glycol 400; 15% (w/w) dimethyl isosorbide; 4% (w/w) water; 5% (w/w) MYRJ® S100-PA-SG; 1% (w/w) butylated hydroxytoluene, and 0.05% caramel colorant.

Yet another embodiment of the pharmaceutical formulation comprises 6% (w/w) of compound I or a pharmaceutically acceptable salt thereof; 35% (w/w) polyethylene glycol 4500; 33.95% (w/w) polyethylene glycol 400; 15% (w/w) dimethyl isosorbide; 4% (w/w) water; 5% (w/w) MYRJ® S100-PA-SG; 1% (w/w) butylated hydroxytoluene, and 0.05% caramel colorant.

A person of ordinary skill in the art will appreciate that the pharmaceutical formulation may also comprise a therapeutically effective amount of an additional or subsequent active agent, or agents. Certain disclosed embodiments of the pharmaceutical formulation comprise a therapeutically effective amount of an additional or subsequent agent suitable for treating cutaneous lupus, such as a topical corticosteroid.

A person of ordinary skill in the art also will appreciate that the pharmaceutical formulation may comprise other agents, such as a fragrance, an absorbent, an astringent, a binder, a buffering agent, a chelating agent, a film-forming agent, a conditioning agent, an opacifying agent, a protectant, or any combination thereof.

Certain embodiments concern a method for treating cutaneous lupus. For example, the method may comprise topically administering to a subject disclosed embodiments of the pharmaceutical formulation. For particular embodiments, the method comprises identifying a subject having cutaneous lupus lesions. A disclosed embodiment, or embodiments, of the pharmaceutical formulation is applied topically to the subject's cutaneous lupus lesions. The disclosed method contemplates using any one of the disclosed embodiments of the pharmaceutical formulation. In particular disclosed embodiments, the method may comprise using a pharmaceutical formulation comprising: 3% (w/w) of compound I or a pharmaceutically acceptable salt thereof; 32% (w/w) polyethylene glycol 4500; 39.95% (w/w) polyethylene glycol 400; 15% (w/w) dimethyl isosorbide; 4% (w/w) water; 5% (w/w) MYRJ® S100-PA-SG; 1% (w/w) butylated hydroxytoluene; and 0.05% caramel colorant. In other particular disclosed embodiments, the method may comprise using a pharmaceutical formulation comprising: 6% (w/w) of compound I or a pharmaceutically acceptable salt thereof; 35% (w/w) polyethylene glycol 4500; 33.95% (w/w) polyethylene glycol 400; 15% (w/w) dimethyl isosorbide; 4% (w/w) water; 5% (w/w) MYRJ® S100-PA-SG; 1% (w/w) butylated hydroxytoluene; and 0.05% caramel colorant.

The foregoing and other objects, features, and advantages of the invention will become more apparent from the following detailed description.

DETAILED DESCRIPTION

Embodiments of topical formulations for administering a compound and methods of using the compound and/or topical formulations thereof in the treatment of dermatological disorders are disclosed. Embodiments of the disclosed topical formulations are suitable for treating cutaneous collagen vascular diseases, such as a cutaneous lupus disorder.

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular foams "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

A. Abbreviations and Trademarks

ACLE: Acute cutaneous lupus erythematosus
API: Active pharmaceutical ingredient
BHA: Butylated hydroxyanisole
BHT: butylated hydroxytoluene
CCLE: Chronic cutaneous lupus erythematosus
COX: Cyclooxygenase
DES: Dry eye syndrome
DILE: Drug induced lupus erythematosus
DLE: Discoid lupus erythematosus
DMI: Dimethyl isosorbide
GMP: Good Manufacturing Practice
EtOH: Ethanol
IPA: Isopropyl alcohol
LE: Lupus erythematosus
Myrj®: Polyoxyl stearate
PEG: Polyethylene glycol
PG: Propylene glycol
RH: Relative humidity
SCLE: Sub-acute cutaneous lupus erythematosus
SLE: Systemic lupus erythematosus
Span®: Sorbitan monostearate
STAT: Signal transducer and activator of transcription
Tefose® 63: PEG-6 stearate, glycol stearate, and PEG-32 stearate
THF: Tetrahydrofuran
TPGS: D-α-tocopheryl polyethylene glycol 1000 succinate

B. Definitions

"Antioxidant" refers to a molecule capable of inhibiting the oxidation of other molecules.

"Corticosteroids" are steroid hormones that are produced in the adrenal cortex. Corticosteroids are involved in a wide range of physiologic systems such as stress response, immune response and regulation of inflammation, carbohydrate metabolism, protein catabolism, blood electrolyte levels, and behavior. Examples of corticosteroids include cortisol, prednisone and prednisilone. Corticosteroids can be administered either orally, parenterally (for example by injection) or by direct topical application to a lesion on the skin, and they may be combined with compound I in a combination formulation. "Topical corticosteroids" are applied topically directly to the skin, but long term use of topical corticosteroids causes unsightly skin atrophy.

"Cutaneous" or "dermal" refers to the skin, which is the tissue forming the outer covering of the vertebrate body. The skin (which is also sometimes referred to as the "integumentary system"), in combination with the mucous membranes (particularly the oral, nasal, oral and eyelid membranes) help protect the body from its external environment. The skin consists of two layers (the dermis and epidermis), the outermost of which may be covered in many animals (including humans) at least in part with hair. It is mainly protective and sensory in function, along with the mucous membranes of the eye, nose and mouth.

"Cutaneous lupus" or "cutaneous lupus erythematosus" refers to cutaneous manifestations of lupus erythematosus according to the Gilliam classification of lupus erythematosus skin disease. Rothfield et al., Clinics in Dermatology 24:348-362 (2006). This system divides lupus skin disease into lupus erythematosus-specific and lupus erythematosus non-specific skin diseases that show distinctive histologic changes.

"Discoid lupus erythematosus" or "DLE" (also known as chronic cutaneous lupus erythematosus or CCLE) is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. Unlike SLE, antibodies against double-stranded DNA (e.g., the DNA-binding test) are almost invariably absent in DLE. In some embodiments of the methods disclosed herein, compound I is used to treat double-strand DNA (ds-DNA) negative DLE subjects.

"Chronic cutaneous lupus erythematosus" (CCLE) is generally subdivided into classic discoid lupus erythematosus (DLE), childhood discoid lupus erythematosus, generalized discoid lupus erythematosus, localized discoid lupus erythematosus, lupus erythematosus profundis, lupus erythematosus panniculitis (lupus erythematosus profundus), mucosal lupus erythematosus, tumid lupus erythematosus, chilblain lupus erythematosus, lupus erythematosus-lichen planus overlap syndrome, verrucous lupus erythematosus (hypertrophic lupus erythematosus) and other rare variants. Classic DLE is the most common form of CCLE, and most patients who have classic DLE lesions never develop features of systemic lupus erythematosus. Classic DLE presents as a well-demarcated red-purple macule of a papule with a superficial scale. The lesion increases in size into a coin-shaped, or discoid, plaque with peripheral hyperpigmentation. Adherent scales extend into dilated hair follicles. The center of the lesion becomes depressed with scarring, depigmentation, and telangiectasia. The plaques may become confluent to form large disfiguring lesions. The hair follicle may become plugged with thick scales, which when peeled back reveal keratotic spikes, which is referred to as the carpet tack sign. Histopathological characteristics include hyperkeratosis and follicular plugging, loss of organized basal epidermis and an atrophic spinous layer. The basal layer may also demonstrate edema, liquefaction, basement membrane thickening, increased melanin pigmentation, and pigment incontinence. A mononuclear cell infiltrate of macrophages and T lymphocytes is found in the dermis, with plasma cells in chronic lesions leading to mucin deposition.

"Drug-induced lupus erythematosus" (DILE) is a variant autoimmune disease that occurs as a side-effect of long term use of certain medications. The symptoms of DILE are similar to those of SLE, and can include fatigue, low-grade fever, loss of appetite, muscles aches, arthritis, ulcers of the mouth and nose, facial rash, unusual sensitivity to sunlight, pleuritis, pericarditis, and Raynaud's phenomenon. The ulcers and rash are examples of cutaneous manifestations of DILE. The symptoms resolve within days to months after withdrawal of the culprit drug in a patient who has no underlying immune system dysfunction. The most common drugs that cause DILE are hydralazine, procainamide, quinidine, isoniazid, diltiazem, and minocycline. Some of these drugs (such as procainamide, chlorpromazine, and quinidine) cause the production of antinuclear antibodies against the histone dimer H2A-H2B. Hydralazine forms antinuclear antibodies to H1 and the H3-H4 complex. DILE generally occurs months to years after drug use begins, in contrast to flares of SLE that occur within hours to days after use of a drug begins.

A diagnosis of DILE is made in a patient who has one or more clinical symptoms of SLE (eg, arthralgias, lymphadenopathy, rash, fever); antinuclear antibodies are present; patient had no history of SLE prior to using the culprit drug; suspect drug was taken anytime from 3 weeks to 2 years prior to the appearance of symptoms; and clinical improvement is rapid when the drug is discontinued, while antinuclear antibodies and other serologic markers slowly decrease toward more normal levels.

"Emollient" refers to a compound that softens or soothes the skin.

"Epithelial surfaces" refers to tissue made up of epithelial cells that cover the surfaces of the body. Epithelial surfaces include external surfaces such as the skin and mucosa of the mouth and nose, as well as the linings of internal body surfaces. "External" epithelial surfaces are those exposed to the surfaces of the body (such as the skin, and the lining of the nose and mouth) and that are accessible to direct application of creams or ointments to the surface without the use of instrumentation (such as endoscopes or scalpels).

"Lupus erythematosus" (LE) is a generic term for a collection of autoimmune diseases. Symptoms of LE may affect many different body systems, including joints, skin, kidneys, blood cells, heart and lungs. LE may manifest as a systemic disease (having both cutaneous and other manifestations) or as a purely cutaneous disease (that affects only the skin). The systemic form of LE is known as systemic lupus erythematosus (SLE). Among the cutaneous forms of LE are acute cutaneous lupus erythematosus, subacute cutaneous lupus erythematosus, and chronic cutaneous lupus erythematosus (discoid lupus, discussed above).

Acute cutaneous lupus erythematosus (ACLE) can be either localized or generalized. Localized ACLE is characterized by erythema over the malar eminences of the face and bridge of the nose (butterfly blush) while the nasolabial folds are typically spared. The ACLE rash may have a fine surface scale and be associated with edema, although particularly severe cases can produce vesiculobullous skin changes. Histopathological changes include sparse dermal cellular infiltrate, focal liquefactive degeneration of the basal epidermis, and upper dermal edema. Epidermal necrosis may occur in the most severe forms.

Subacute cutaneous lupus erythematosus (SCLE) is subdivided into two morphological variants: annular SCLE and papulosquamous SCLE. Annular SCLE has also been referred to as lupus marginatus, symmetrical erythema centrifugum, autoimmune annular erythema, and lupus erythematosus gyratum repens. SCLE presents with erythematous macules and papules that subsequently develop into papulosquamous or annular plaques. Most patients will tend to develop predominantly one type of lesion, although some will display the elements of both simultaneously. SCLE is very photosensitive, with lesions most commonly on the neck and upper chest, upper back, shoulders, extensor surfaces of the arms and forearms, and dorsum of the hands (knuckles are typically spared). The face and scalp are uncommonly involved. Histopathological features include hyperkeratosis, degeneration of the basal cell layer, and a mononuclear cell infiltrate in the dermal-epidermal junction and dermis.

"Mucous membranes" (or "mucosa") are linings of mostly endodermal origin, covered in epithelium, which are involved in absorption and secretion. They line cavities that are exposed to the external environment and internal organs. They are continuous with skin at several locations, such as the nostrils, mouth, lips, eyelids, ears, genital area, and anus.

"Non-steroidal anti-inflammatory drug (NSAID)" is a type of anti-inflammatory agent that works by inhibiting the production of prostaglandins. NSAIDS exert anti-inflammatory, analgesic and antipyretic actions. Examples of NSAIDS include ibuprofen, ketoprofen, piroxicam, naproxen, sulindac, aspirin, choline subsalicylate, diflunisal, fenoprofen, indomethacin, meclofenamate, salsalate, tolmetin and magnesium salicylate. These agents can be administered either orally, parenterally (for example by injection) or by direct topical application to an inflamed area, and they may be combined with compound I in a combination formulation.

"Penetration enhancer" refers to a compound that improves drug delivery into the skin.

"Pharmaceutically acceptable salt" refers to a biologically compatible salt of a compound that can be used as a drug, which salts are derived from a variety of organic and inorganic counter ions well known in the art.

"Pharmaceutically effective amount" or "therapeutically effective amount" refers to an amount of a compound sufficient to treat a specified disorder or disease or one or more of its symptoms and/or to prevent the occurrence of the disease or disorder. "Treatment" includes arresting further advancement of a disease, as well as reversing the disorder, inducing regression of lesions, or in some examples curing the disorder.

As used herein, the phrase "significantly decreases DLE lesions" means a statistically significant (such as $p<0.05$) decrease in DLE lesions as measured by standard dermatologic practice. For example, a decrease in DLE lesions can be assessed by counting the number of treated lesions, or the total surface area of a treated lesion or lesions.

"Subject" refers to humans and non-human subjects.

"Surfactant" refers to a compound that reduces surface tension when dissolved in water or water-based solutions, or that reduces interfacial tension between two liquids. A surfactant molecule typically has a polar or ionic "head" and a nonpolar hydrocarbon "tail."

"Systemic lupus erythematosus" or "SLE" is an inflammatory autoimmune disorder that occurs predominantly in women, and is characterized variously by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE.

"Topical" delivery refers to application of a drug-containing formulation to the skin to directly treat cutaneous disorders or the cutaneous manifestations of a disease with the intent of substantially directing the pharmacological effect of the drug to the surface of the skin or within the skin. Topical dosage forms are typically semi-solid systems, but can include a variety of other dosage forms such as foams, sprays, medicated powders, solutions and medicated adhesive systems. Topical delivery includes external topical agents that are spread, sprayed, or otherwise dispersed on cutaneous tissues to cover the affected area, or internal topical agents that are applied to the mucous membranes orally, vaginally, or on anorectal tissues for local activity. The topical drugs disclosed herein can be administered in any topical dosage form, for example as a solid (powder, aerosol or plaster); liquid (lotion, liniment, solution, emulsion, suspension, aerosol) or semi-solid (ointment, cream, paste, gel, jelly or suppository).

"Topical base" refers to the solid component of a topical formulation. A therapeutically effective amount of an active compound is combined with a topical base to produce a topical formulation such as an ointment, a cream, or a lotion. The topical formulation also may include additional components such as excipients, including, without limitation, antioxidants, binders, emollients, penetration enhancers, surfactants, and the like.

II. PHARMACEUTICAL COMPOSITIONS

Embodiments of the disclosed topical pharmaceutical compositions include compound I or a pharmaceutically acceptable salt or solvate thereof. Compound I is a JAK3 and Syk kinase inhibitor with water solubility of 2 μg/mL at 25° C. Compound I is also referred to as N2-(3-aminosulfonyl-4-methylphenyl)-5-fluoro-N4-[4-(prop-2-ynyloxy) phenyl]-2,4-pyrimidinediamine.

Compound I

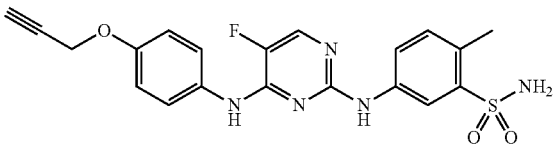

For the purposes of brevity in description, whenever compound I is referred to in an embodiment, the embodiment also includes a salt form of compound I.

One of ordinary skill in the art will appreciate that compound I may exhibit the phenomena of tautomerism, conformational isomerism and/or geometric isomerism. It should be understood that the invention encompasses any tautomeric, conformational isomeric and/or geometric isomeric forms of compound I as well as mixtures of these various different isomeric forms. The invention also is meant to encompass atropisomers. Compound I may be in the form of a salt. Such salts include salts suitable for pharmaceutical uses ("pharmaceutically-acceptable salts"), salts suitable for veterinary uses, and the like. Such salts may be derived from acids or bases, as is well-known in the art. Because compound I has basic groups, for example pyrimidine nitrogen atoms, and/or the nitrogen atoms at N2 and N4 of the pyrimidinediamine system, this compound can form pharmaceutically acceptable acid addition salts.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (for example, hydrochloric acid, hydrobromic acid, hydroiodic acid, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (for example, methanesulfonic acid, ethanesulfonic acid, 1,2-ethane-disulfonic acid, 2-hydroxyethanesulfonic acid, etc.), arylsulfonic acids (for example, benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (for example, an alkali metal ion, an alkaline earth metal ion or an aluminum ion) or coordinates with an organic base (for example, ethanolamine, diethanolamine, triethanolamine, N-methylglucamine, morpholine, piperidine, dimethylamine, diethylamine, triethylamine, ammonia, etc.).

The pharmaceutically acceptable salts described herein may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin. In some embodiments, the salt is a hydrochloride salt or a besylate salt.

Compound I, as well as the salts thereof, may also be in the form of solvates, for example hydrates, and N-oxides, as are well-known in the art.

The pharmaceutical compositions for the administration of compound I may conveniently be presented in dosage unit form and may be prepared by any of the methods well known in the art of pharmacy. The pharmaceutical compositions can be, for example, prepared by uniformly and intimately bringing the active ingredient into association with a liquid carrier or a finely divided solid carrier or both, and placing it in appropriate packaging. For example, in topical formulations of the disclosed compounds, the formulation is placed in an appropriate container (such as a squeeze-tube with a cap for dispensing ointments and creams). Alternatively, the dispenser may include a device for dispensing unit dosages of the drug (such as a bottle or dropper that dispenses a controlled pre-determined dosage of the drug to a target area). In the pharmaceutical composition, compound I is included in an amount sufficient to produce the desired therapeutic effect.

For topical administration, compound I may be formulated as a solution, gel, ointment, cream, suspension, etc. as are well-known in the art. In addition to being suitable for administration to the skin, some embodiments of the solutions, gels, ointments, creams and suspensions are also well-suited for administration directly to the eye. One embodiment is a pharmaceutical formulation comprising compound I, where the formulation is selected from a solution, a gel, an ointment, a cream and a suspension. In one aspect, such formulations formulated for topical administration, include a therapeutically effective amount of a compound I or a pharmaceutically acceptable salt thereof, such as a hydrochloride salt or a besylate salt. Particular embodiments of formulations for use in the methods described herein include a therapeutically effective amount of the compound, a topical base, an antioxidant, an emollient, and an emulsifier. A person of skill in the art will appreciate that a therapeutically effective amount of the compound may vary, but typically the therapeutically effective amount is from 0.1% to 10% (w/w).

The topical base may comprise polyethylene glycol having a selected molecular weight. Particular embodiments comprise a polyethylene glycol having a molecular weight of from 3000 to 8000 daltons as a topical base.

In certain embodiments, the formulation is an ointment, and may further include a water-miscible solvent, such as a polyalkylene glycol having an average molecular weight of from 200 daltons to 600 daltons. In certain embodiments the water-miscible solvent comprises PEG-400, and even more particularly PEG-400 substantially free of impurities. In certain embodiments, PEG-400 substantially free of impurities comprises less than 65 ppm formaldehyde, less than 10 ppm formaldehyde, or 1 ppm or less formaldehyde.

Topical formulations for use as described herein also can include a penetration enhancer, such as dimethyl isosorbide, propylene glycol, or combinations thereof; an emollient, such as water; a surfactant, such as sorbitan monostearate, a polyethylene glycol monostearate, D-α-tocopheryl polyethylene glycol 1000 succinate, a composition comprising glycol stearate/PEG32 stearate/PEG6 stearate, and combinations of surfactants; an antioxidant, such as butylated hydroxyanisole, butylated hydroxytoluene, ascorbic acid, a tocopherol, and combinations thereof, with particular embodiments comprising butylated hydroxytoluene as an antioxidant; and an optional colorant, such as 0.05% to 0.25% (w/w) caramel colorant.

In one embodiment, the formulation is a solution. In another embodiment, the formulation is a gel. In another embodiment, the formulation is a suspension. In yet another embodiment, the formulation is a cream or ointment. In one embodiment, the formulation is a liquid, for example, a homogeneous liquid or a suspension, sold in a bottle which dispenses the formulation as drops or a liquid film (for example, from an applicator tip that contacts a target area of the skin to dispense the liquid substantially only on a target area of the skin to be treated). In one embodiment, the formulation is a cream or ointment, sold in a tube which dispenses the formulation to a target area of the skin. In another embodiment, the compound is provided in a viscous liquid (such as carboxylmethylcellulose, hydroxypropylmethycellulose, polyethylene glycol, glycerin, polyvinyl alcohol, or oil containing drops) for rubbing into the skin or instilling in the eye. The formulations may have preservatives or be preservative-free (for example in a single-use container). One embodiment is any of the aforementioned formulations in a kit for topical or local administration.

Topical formulations comprising compound I optionally may comprise additional pharmaceutically acceptable ingredients such as diluents, stabilizers and/or adjuvants. In certain embodiments, the topical formulations are formulated for the treatment of skin diseases and/or disorders, such as cutaneous lupus, for example chronic cutaneous lupus, such as DLE.

Topical formulations for skin administration disclosed herein contain a pharmaceutically effective amount of compound I, such as from 0.0001% to 10.0% or more by weight. In certain formulations, the pharmaceutically effective amount of the compound is 0.1% to 10% (w/w), such as from 0.2% to 6% (w/w). In other examples, the compound is present in at least 0.2%, 1%, 2%, 3%, 4%, 5%, or 6% (w/w).

Embodiments of topical formulations comprising compound I may include one or more excipients selected from solvents, topical bases, surfactants/emulsifiers, penetration enhancers, emollients, antioxidants, color additives, and any combination thereof. Methods of formulating and testing drugs for topical application are described, for example, in Remington, The Science and Practice of Pharmacy (21$^{st}$ edition), pages 872-882 (2006).

Topical bases include, but are not limited to, hydrophobic vehicles such as hydrocarbons, liquid petrolatum (mineral oil, liquid paraffin, paraffin oil), white petrolatum (petroleum jelly, VASELINE®), yellow petrolatum (petroleum jelly), squalane (perhydrosqualene, spinacane), and silicones; silicones such as liquid polydimethylsiloxanes (dimethicone, silastic, medical grade silicone oil), alcohols such as lauryl alcohols (1-dodecanol, dodecyl alcohols), myristyl alcohols (tetradecanol, tetradecyl alcohols), cetyl alcohols (hexadecanol, ethal, palmityl alcohols), stearyl alcohols (stenol, cetosteryl alcohols), oleyl alcohols (ocenol); sterols such as sterol esters; lanolin such as hydrous wool fat, lanum; anhydrous lanolin (such as wool fat, anhydrous lanum, agnin); semi synthetic lanolins; carboxylic acids such as lauric acid, myristic acid, palmitic acid, stearic acid, oleic acid; esters and polyesters, such as cholesterol esters (stearate), ethylene glycol monoesters, propylene glycol monoesters, glyceryl monoesters, glyceryl monostearate, sorbitol monoesters, sorbitan monoesters, sorbitol diesters, sorbitan polyesters (spans, arlacels), glyceryl tristearate, lard, almond oil, corn oil, castor oil, cottonseed oil, olive oil, soybean oil, hydrogenated oils, sulfated oils, isopropyl myristate, isopropyl palmitate; and ethers and polyethers (polydisperse or monodisperse), such as polyethylene glycols or polypropylene glycols (pluronics).

Water-miscible solvents that may be used include polyols and polyglycols such as propylene glycol (1,2-propanediol), glycerin (glycerol), liquid polyethylene glycol, solid polyethylene glycol (hard macrogol, Carbowax®), glycol furol, 1,2-phenol-hexanetriol, sorbitol solution, esters and polyesters such as polyoxyethylene sorbitan monoesters (e.g., Tween® 60) and polyoxy ethylene sorbitan polyesters (e.g., Tween® 20), ethers and polyethers such as polyethylene glycol mono-cetyl ether (cetomacrogol 1000) and polyethylene-polypropylene glycols (pluronics). In one embodiment, the water-miscible solvent includes PEG-400. Surprisingly, use of standard GMP quality PEG-400 was found to introduce impurities into the formulation. Without being limited to any particular theory it currently is believed that trace amounts of formaldehyde in the PEG-400 reacted with compound I. Disclosed herein are formulations including PEG-400 substantially free of impurities, such as PEG-400 having less than about 65 ppm formaldehyde, such as less than about 10 ppm formaldehyde or about 1 ppm or less formaldehyde.

Suitable surfactants include, but are not limited to a sterol or sterol ester, for example cholesterol (cholesterin), lanolin (hydrous wool fat, lanum), anhydrous lanolin (wool fat, anhydrous lanum, agnin), or semi synthetic lanolin; carboxylic acids such as $Na^+$, $K^+$, ethanolamine salts of lauric acid, myristic acid, palmitic acid, stearic acid, oleic acid, or an ether or polyether such as polyethylene-polypropylene glycols (pluronics). If an oil-in-water (o/w) emulsifier is desired, the following examples may be used: esters and polyesters such as polyoxyethylene, sorbitan monoesters (Span™ 20, Span™ 40, Span™ 80), polyoxy ethylene esters (stearate-polyethylene glycol monoesters, Myrj® 45, Myrj® 59), polyoxy ethylene sorbitan polyesters (tweens); ethers and polyethers such as polyethylene glycol monocetyl ether (cetomacrogol 1000) or polyethylene-polypropylene glycols (pluronics), and others such as sodium lauryl sulfate, borax (sodium borate), ethanolamine, or triethanolamine. Nonionic surfactants, like Surfactant 190 (dimethicone copolyol), Polysorbate 20 (Tween® 20), Polysorbate 40 (Tween® 40), Polysorbate 60 (Tween® 60), Polysorbate 80 (Tween® 80), lauramide DEA, cocamide DEA, and cocamide MEA, amphoteric surfactants like oleyl betaine and cocamidopropyl betaine (Velvetex® BK-35), and cationic surfactants, like Phospholipid PTC (Cocamidopropyl phosphatidyl PG-dimonium chloride), can be used. Appropriate combinations or mixtures of such surfactants may also be used.

Penetration enhancers improve drug delivery into the skin. Suitable penetration enhancers include, but are not limited to, alcohol, alkyl methyl sulfoxide, pyrrolidone, laurocapram, dimethyl formamide, tetrahydrofurfuryl alcohol, an amphiphile, or other miscellaneous enhancers such as clofibric acid amide, hexamethylene lauramide, dimethyl isosorbide, propylene glycol, proteolytic enzymes, terpenes or sesquiterpenes.

Suitable moisturizers for use in the formulations of compound I include, but are not limited to, lactic acid and other hydroxy acids and their salts, glycerin, propylene glycol, butylene glycol, sodium PCA, Carbowax® 200, Carbowax® 400, and Carbowax® 800. Suitable emollients for use in the formulations include, but are not limited to, water, PPG-15 stearyl ether, lanolin alcohol, lanolin, lanolin derivatives, cholesterol, petrolatum, isostearyl neopentanoate, octyl stearate, mineral oil, isocetyl stearate, Ceraphyl® 424 (myristyl myristate), octyl dodecanol, dimethicone (Dow Corning 200-100 cps), phenyl trimethicone (Dow Corning 556), Dow Corning 1401 (cyclomethicone and dimethiconol), and cyclomethicone (Dow Corning 344), and Miglyol® 840 (manufactured by Huls; propylene glycol dicaprylate/dicaprate). In addition, appropriate combinations and mixtures of any of these moisturizing agents and emollients may be used.

The composition may also include preservatives, antimicrobials, and/or antioxidants, such as benzalkonium chloride, benzoic acid, benzyl alcohol, bronopol, chlorhexidine, chlorocresol, imidazolidinyl urea, paraben esters, phenol, phenoxyethanol, potassium sorbate, or sorbic acid; antioxidants such as α-tocopherol, ascorbic acid, ascorbyl palmitate, butylated hydroxyanisole, butylated hydroxytoluene, sodium ascorbate, sodium metabisulfite; chelating agents such as citric acid or edetic acid; buffers such as citric acid and salts, phosphoric acid and salts, $H_3PO_4/NaH_2PO_4$, glycine, acetic acid, triethanolamine, or boric acid; humectants such as glycerin (glycerol), propylene glycol (E1520), glyceryl triacetate (E1518), sorbitol (E420), xylitol and malitol (E965), polydextrose (E1200), quillaia (E999), lactic acid, urea or lithium chloride; and/or a sequestering antioxidant such as citric acid and it salts ethylenediaminetetraacetic acid (Versene®, EDTA).

The composition further may include dyes/colorants and/or fragrances. Suitable fragrances and colors, such as caramel, FD&C Red No. 40 and FD&C Yellow No. 5, may be used in the formulations. Other examples of fragrances and colors suitable for use in topical products are known in the art.

Other suitable additional and adjunct ingredients which may be included in the formulations include, but are not limited to, absorbents (e.g., hydrogels), astringents (e.g., witch hazel, alcohol, and herbal extracts such as chamomile extract), binders (e.g., starch, cellulose ethers, microcrystalline cellulose, calcium hydrogen phosphate, calcium phosphate dibasic, and calcium sulfate dihydrate), other excipients (e.g., polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose), buffering agents (e.g., monobasic or dibasic potassium phosphate, monobasic or dibasic sodium phosphate, magnesium hydroxide), chelating agents (e.g., EDTA (ethylenediaminetetraacetic acid, tetrasodium salt)), film-forming agents (e.g., chitosan, hydroxypropylmethylcellulose, polyvinyl alcohol), conditioning agents (e.g., petrolatum, glycerin, propylene glycol), opacifying agents (e.g., titanium dioxide), pH adjusters (e.g., citric acid and sodium hydroxide), and protectants. Examples of each of these ingredients, as well as examples of other suitable ingredients in topical product formulations, may be found in publications by The Cosmetic, Toiletry, and Fragrance Association (CTFA). See, e.g., CTFA Cosmetic Ingredient Handbook, 2nd edition, eds. John A. Wenninger and G. N. McEwen, Jr. (CTFA, 1992).

A particular embodiment of the topical treatment may be an ointment, which is a semisolid preparation intended for external application to the skin or mucous membranes. In a specific example, the ointment is based on petrolatum. The ointment does not contain sufficient water to separate into a second phase at room temperature. A water-soluble ointment may be formulated with polyethylene glycol. Ointments are ideal emollients with good skin penetration and adherence to surfaces. The ointment is in a convenient container such as a tube or jars.

Alternatively, the topical dosage form is a cream in which the compounds are dissolved or suspended in water removable or emollient bases. The creams may be either water-in-oil or oil-in-water compositions. Immiscible compounds may be combined by mechanical agitation or heat using wet gum, dry gum, bottle, and beaker methods. In some embodiments, the cream is an oil-in-water emulsion or aqueous microcrystalline dispersion of long chain fatty acids or alcohols that are water washable and more cosmetically and aesthetically acceptable.

In other embodiments, the active ingredients are provided for administration in a paste, which can be considered an ointment into which a high percentage of insoluble solids have been added, for example as much as 50% by weight. The paste is much stiffer than the ointment due to the presence of solids, which form a particulate matrix over and above the ointment structure already present. Ingredients such as starch, zinc oxide, calcium carbonate, and talc are used as the solid phase. Pastes provide a particularly good protective barrier on skin. Like ointment, a paste forms an unbroken, relatively water impermeable film on the skin surface; unlike ointment the film is opaque and therefore an effective sun filter. Thus, pastes are particularly effective for protecting the skin from ultraviolet radiation that may worsen the condition being treated (such as DLE).

In yet other embodiments, the active agent is provided in a gel, jelly or lotion. Gels are semisolid systems consisting of dispersions of small or large molecules in an aqueous liquid vehicle rendering jelly-like through the addition of gelling agent. Among the gelling agents used are synthetic macromolecules, such as carbomer 934, and cellulose derivatives, such as carboxymethylcellulose or hydroxypropylmethylcellulose. Gels are compatible with many substances and may contain penetration enhancers to improve delivery into the skin. The gels may be either single-phase gels in which the macromolecules are uniformly distributed throughout a liquid with no apparent boundaries between the dispersed macromolecules and the liquid, or double-phase gels in which the gel mass consists of floccules of small distinct particles, often referred to as a magmas. A jelly contains a water-soluble base prepared from natural gums such as tragacanth, pectin, alginate, or boroglycerin, or from synthetic derivatives of a natural substance such as methylcellulose or carboxymethylcellulose. A lotion is a clear solution containing 25-50% alcohol, which optionally contains an antiseptic, or mollient. Other optional ingredients that may be added to the lotion are an extract of witchhazel, menthol, glycerin, boric acid, alum, or potassium oxyquinoline.

Some embodiments of the disclosed topical formulation include a therapeutically effective amount of compound I, or a pharmaceutically acceptable salt thereof. In certain embodiments, the therapeutically effective amount is up to about 10% (w/w) of the formulation, such as from about 0.1 to about 10% (w/w), from 0.2% to 6% (w/w), or from 1% to 6% (w/w) compound I, or a pharmaceutically acceptable salt thereof.

Embodiments of the disclosed topical formulation may include a topical base, a water-miscible solvent, a penetration enhancer, an emollient, a surfactant, an antioxidant, a colorant, or any combination thereof. In some embodiments, the pharmaceutical formulation includes from 0.2% to 10% (w/w) compound I or a pharmaceutically acceptable salt thereof, from 15% to 25% (w/w) topical base, from 40% to 50% (w/w) water-miscible solvent, from 10% to 20% (w/w) penetration enhancer, from 5% to 15% (w/w) emollient, from 3% to 7% (w/w) surfactant, from 0.5% to 1.5% (w/w) antioxidant, and optionally from 0.05% to 0.25% (w/w) colorant. In one embodiment, the topical formulation consists essentially of from 0.2% to 10% (w/w) compound I, or a pharmaceutically acceptable salt thereof, from 15% to 25% (w/w) topical base, from 40% to 50% (w/w) water-miscible solvent, from 10% to 20% (w/w) penetration enhancer, from 5% to 15% (w/w) emollient, from 3% to 7% (w/w) surfactant, and from 0.5% to 1.5% (w/w) antioxidant. In other embodiments, the pharmaceutical formulation includes from 0.1% to 10% (w/w) compound I or a pharmaceutically acceptable salt thereof, from 15% to 40% (w/w) topical base, from 25% to 50% (w/w) water-miscible solvent, from 10% to 20% (w/w) penetration enhancer, from 3% to 15% (w/w) emollient, from 3% to 9% (w/w) surfactant, from 0.5% to 1.5% (w/w) antioxidant, and optionally from 0.05% to 0.25% (w/w) colorant.

In some embodiments, the topical base is selected from polyethers such as polyalkylene glycols. Suitable polyalkylene glycols include polyethylene glycols (e.g., PEG with an average molecular weight ranging from 3000-8000 daltons).

The polyethylene glycol may be polydisperse or monodisperse. The water-miscible solvent may be a polyether such as a liquid polyalkylene glycol (e.g., PEG with an average molecular weight ranging from 200-600 daltons). In certain embodiments, the penetration enhancer is dimethyl isosorbide (DMI), propylene glycol, or a combination thereof. In some embodiments, the emollient is water. Suitable surfactants include Tefose® 63 (glycol stearate, PEG32 stearate, PEG6 stearate), Span® (sorbitan monostearate), Myrj® (polyethylene glycol monostearate, $C_{18}H_{35}O_2(C_2H_4O)_nH$), or TPGS (D-α-tocopheryl polyethylene glycol 1000 succinate). In some embodiments, the antioxidant is BHT (butylated hydroxytoluene). Caramel may be added as a colorant.

In some embodiments, the topical formulation comprises from 0.2% to 6% (w/w) compound I (or a pharmaceutically acceptable salt thereof), 20% (w/w) topical base, from 43% to 48.8% (w/w) water-miscible solvent, 15% (w/w) penetration enhancer, 10% (w/w) emollient, 5% (w/w) surfactant, 1% (w/w) antioxidant, and optionally 0.05-0.2% (w/w) colorant. In certain embodiments, the topical formulation comprises from 1% to 6% (w/w) compound I, 20% (w/w) PEG4500, from 43% to 48% (w/w) PEG400, 15% (w/w) DMI, 10% (w/w) $H_2O$, 5% (w/w) Myrj®59 (polyethylene glycol monostearate), 1% (w/w) BHT, and optionally from 0.05% to 0.1% (w/w) caramel. In one embodiment, the topical formulation consists essentially of from 1% to 6% (w/w) compound I, 20% (w/w) PEG4500, from 43% to 48% (w/w) PEG400, 15% (w/w) DMI, 10% (w/w) $H_2O$, 5% (w/w) Myrj®59 (polyethylene glycol monostearate), and 1% (w/w) BHT. In other disclosed embodiments, the pharmaceutical formulation comprises from 0.2% to 6% (w/w) of compound I or a pharmaceutically acceptable salt thereof; from 30% to 40% or 25% to 40% (w/w) polyethylene glycol with an average molecular weight of from 4000 to 5000 daltons; from 30% to 40% or from 30% to 45% (w/w) polyethylene glycol with an average molecular weight of from 300 to 500 daltons; 15% (w/w) dimethyl isosorbide; from 3% to 5% (w/w) water; 5% (w/w) polyethylene glycol mono stearate; 1% (w/w) butylated hydroxytoluene, and 0.05% caramel colorant.

In one embodiment, the topical formulation comprises 1% (w/w) compound I, 20% (w/w) PEG4500, 48% (w/w) PEG400, 15% (w/w) DMI, 10% (w/w) $H_2O$, 5% (w/w) Myrj® 59, and 1% (w/w) BHT, and 0.05% caramel colorant. In another embodiment, the topical formulation comprises 3% (w/w) compound I, 20% (w/w) PEG4500, 46% (w/w) PEG400, 15% (w/w) DMI, 10% (w/w) $H_2O$, 5% (w/w) Myrj® 59, and 1% (w/w) BHT. In yet another embodiment, the topical formulation comprises 6% (w/w) compound I, 20% (w/w) PEG4500, 43% (w/w) PEG400, 15% (w/w) DMI, 10% (w/w) $H_2O$, 5% (w/w) Myrj® 59, and 1% (w/w) BHT.

In another embodiment, the topical formulation comprises 3% (w/w) of compound I or a pharmaceutically acceptable salt thereof; 32% (w/w) PEG4500; 39.95% (w/w) PEG400; 15% (w/w) dimethyl isosorbide; 4% (w/w) water; 5% (w/w) Myrj® S100-PA-SG; 1% (w/w) butylated hydroxytoluene, and 0.05% caramel.

Yet another embodiment, the topical formulation comprises 6% (w/w) of compound I or a pharmaceutically acceptable salt thereof; 35% (w/w) PEG4500; from 33.95% (w/w) PEG400; 15% (w/w) dimethyl isosorbide; 4% (w/w) water; 5% (w/w) Myrj® S100-PA-SG; 1% (w/w) butylated hydroxytoluene, and 0.05% caramel colorant.

III. METHODS OF USE

A. Use of Topical Formulations

The present disclosure provides embodiments of topical formulations including compound I, salts, and solvates thereof, for use in treating diseases and/or disorders of the skin and/or mucous membranes, and in particular lesions caused by cutaneous lupus. Compound I may be administered alone or in combination with other agents. As described, compound I can be administered as the parent and/or the salt form, and as pharmaceutical formulations thereof.

As used herein, and as well understood in the art, "treatment" is an approach for obtaining beneficial or desired results, including clinical results. For the purposes of this disclosure, beneficial or desired results can include one or more, but are not limited to, alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease, state, and remission (whether partial or total), whether detectable or undetectable. Compound I is potent and can be administered locally (for example topically or by injection to the skin or mucous membrane) at very low doses, thus minimizing systemic adverse effects. It is believed that this treatment also avoids the side-effects caused by more standard treatments (such as corticosteroids), and is highly effective because of its direct application to affected areas.

Compound I is a potent and selective inhibitor JAK1/3-dependent cytokine signaling operative in T- and B-cells and Syk-dependent signaling in macrophages, dendritic cells, and B-cells. For example, Compound I has a half maximal effective concentration (EC50) in human cell based assays against JAK3 and Syk in the range of 0.18 μM and 0.14 μM, respectively, and has little or no activity on other cytokine (IL-1β and TNFα) or receptor tyrosine kinase (RTK) signaling, and is not a broad inhibitor of cell proliferation. Compound I is particularly selective for cytokine signaling pathways containing JAK3. As a consequence of this activity, compound I may be used in a variety of in vitro, in vivo and ex vivo contexts to regulate or inhibit JAK kinase activity, signaling cascades in which JAK kinases play a role, and the biological responses effected by such signaling cascades. For example, in one embodiment, compound I may be used to inhibit JAK kinase, either in vitro or in vivo, in virtually any cell type expressing the JAK kinase (such as hematopoietic cells). It may also be used to regulate signal transduction cascades in which JAK kinases, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15 and IL-21 receptor signaling cascades. Compound I may also be used in vitro or in vivo to regulate, and in particular inhibit, cellular or biological responses affected by such JAK-dependent signal transduction cascades. Such cellular or biological responses include, but are not limited to, IL-4/ramos CD23 upregulation, IL-2 mediated T-cell proliferation, etc. Importantly, compound I may be used to inhibit JAK kinases in vivo as a therapeutic approach towards the treatment or prevention of diseases mediated, either wholly or in part, by a JAK kinase activity. Such diseases are referred to as "JAK kinase mediated diseases."

While not wishing to be bound by a single theory, it is currently believed that compound I is an effective treatment of cutaneous disorders due, at least in part, to its JAK inhibitory activity. Examples of cutaneous diseases that are mediated, at least in part, by JAK kinases that can be treated or prevented according to embodiments of the disclosed methods include diseases and disorders of the skin or mucous membranes including, but not limited to, the lesions of cutaneous lupus such as DLE, ACLE, SCLE or DILE that are present on the skin and mucous membranes. However, as a result of the aforementioned activities, although methods described herein are directed to treatment of skin and mucous membrane disorders, administration of compound I and/or formulations thereof may carry other therapeutic benefit, that is, in other tissues or organs of the body. One embodiment is a method of treating a disorder or disease of the skin or mucous membranes (such as DLE, ACLE, SCLE or DILE), where a secondary benefit is also realized. For example, application of compound I to DLE lesions on the eyelid can also serve as an effective treatment for dry eyes, dry eye syndrome, uveitis, allergic conjunctivitis, glaucoma or rosacea (of the eye). Dry eye syndrome (DES), otherwise known as keratoconjunctivitis sicca (KCS), keratitis sicca, sicca syndrome, or xerophthalmia, is an eye disease caused by decreased tear production or increased tear film evaporation commonly found in humans and some animals. Uveitis or iridocyclitis refers to inflammation of the middle layer of the eye (the "uvea") and in common usage may refer to any inflammatory process involving the interior of the eye. Allergic conjunctivitis is inflammation of the conjunctiva (the membrane covering the white part of the eye) due to allergy. Glaucoma refers to a group of diseases that affect the optic nerve and involves a loss of retinal ganglion cells in a characteristic pattern, i.e., a type of optic neuropathy. Raised intraocular pressure is a significant risk factor for developing glaucoma (above 22 mmHg or 2.9 kPa), and inflammatory processes, e.g. uveitis, can cause this rise in intraocular pressure.

The disclosed treatment for DLE, ACLS, SCLE or DILE can also treat the symptoms of rosacea, which is a chronic inflammatory condition characterized by facial erythema that can also affect the eyes and nose (rhinophyma).

In one embodiment, compound I is used to treat any of the aforementioned ocular diseases and/or disorders in combination with treating cutaneous lupus. In one embodiment, compound I is employed as a salt form, e.g., as a hydrochloride or besylate salt.

Compound I, or pharmaceutical compositions thereof, will generally be used in an amount effective to achieve the intended result, for example in an amount effective to treat the subject's particular condition. The compound is administered to achieve a therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from a form of cutaneous lupus, such as DLE, provides therapeutic benefit not only when the underlying dermal lesion is eradicated or ameliorated, but also when the patient reports a decrease in the severity or duration of the symptoms associated with the cutaneous lupus. Therapeutic benefit also includes halting or slowing the progression of the disease, regardless of whether improvement in symptoms is realized.

The amount of compound I administered will depend upon a variety of factors, including, for example, the particular condition being treated, the mode of administration, the severity of the condition being treated, the age of the patient, etc. Determination of an effective dosage is well within the capabilities of those skilled in the art. A skilled practitioner will be able to determine the optimal dose for a particular individual. Effective dosages may be estimated initially from in vitro assays. For example, an initial dosage for use in animals may be formulated to achieve a circulating blood or serum concentration of compound I that is at or above an $IC_{50}$ of the particular compound as measured in an in vitro assay, such as the in vitro assays described in Examples 5 and 6 herein. Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, Chapter 1, pp. 1-46, latest edition, Pergamon Press, and the references cited therein.

Initial dosages can also be estimated from in vivo data using animal models, such as those disclosed in Example 7. Animal models useful for testing the efficacy of compounds to treat the various diseases described above are well-known in the art. In cases of local administration, such as local topical administration, the effective local concentration of active compound(s) may not be related to plasma concentration. Skilled artisans will be able to optimize effective local dosages without undue experimentation. In view of the much higher therapeutic index of topical administration to the skin, dosages can be increased beyond general systemic dosages without significant additional concern for side-effects and toxicities. For topical or ocular administration, effective dosages may be those where no significant systemic circulation of the compounds results from administration to the skin or eye, for example, where a topical formulation is applied directly to a cutaneous lesion and a very localized dose is utilized.

B. Co-Administration

When used to treat lesions of the skin and/or mucous membranes, compound I may be administered singly or in combination with other agents useful for treating diseases and/or disorders of the skin. Compound I may be administered in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, -agonists, tryptase inhibitors, aspirin, cyclooxygenase (COX) inhibitors, methotrexate, anti-TNF drugs, rituxan, PD4 inhibitors, p38 inhibitors, PDE4 inhibitors, and antihistamines, to name a few. Compound I may be administered per se or as a pharmaceutical composition comprising the active compound.

The pharmaceutical compositions disclosed herein can be co-administered (concurrently or sequentially) with a variety of other treatments applied to the skin, for example antibacterials (such as BACTROBAN® or CLEOCIN®); antipsoriasis medications (such as Micanol®); antifungal agents (such as LAMISIL®, LOTRIMIN®, and NIZORAL®); acne treatments (such as benzoyl peroxide topical preparations); treatments for seborrheic dermatitis (such as coal tar); corticosteroids; retinoids (such as Retin-A and Tazorac®) which are gels or creams derived from vitamin A that are used to treat conditions including acne; and wart treatments (such as salicylic acid). Any of these agents can be provided in topical or cosmetic formulations, for example in lotions, ointments, creams, gels, soaps, shampoos, or adherent applicators, such as patches.

The pharmaceutical compositions disclosed herein can also be co-administered (concurrently or sequentially) with a variety of other treatments that are not applied to the skin, for example treatments that are administered systemically, for example orally or parenterally. Examples of such systemic treatments include other anti-lupus drugs (such as hydroxychloroquine (PLAQUENIL®), corticosteroids (such as Prednisone), antibiotics (such as erythromycin, tetracycline, and dicloxacillin), antifungal agents (such as ketoconazole and DIFLUCAN®), antiviral agents (such as VALTREX®, acyclovir, and FAMVIR®), corticosteroids, immunosuppressants (such as CYTOXAN®, azathioprine, methotrexate, mycophenolate), and biologics (such as RITUXAN®, ENBREL®, HUMIRA®, REMICADE®, STELARA®, and AMEVIVE®).

Particular immunosuppressive therapies that can be used in combination with compound I include, for example, mercaptopurine, corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies, for example, antilymphocyte globulin (ALG), antithymocyte globulin (ATG), monoclonal anti-T-cell antibodies (OKT3) and irradiation. These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference. Azathioprine is currently available from Salix Pharmaceuticals, Inc. under the brand name AZASAN®; mercaptopurine is currently available from Gate Pharmaceuticals, Inc. under the brand name PURINETHOL®; prednisone and prednisolone are currently available from Roxane Laboratories, Inc.; methyl prednisolone is currently available from Pfizer; sirolimus (rapamycin) is currently available from Wyeth-Ayerst under the brand name RAPAMUNE®; tacrolimus is currently available from Fujisawa under the brand name PROGRAF®; cyclosporine is current available from Novartis under the brand dame SANDIMMUNE® and Abbott under the brand name GENGRAF®; IMPDH inhibitors such as mycophenolate mofetil and mycophenolic acid are currently available from Roche under the brand name CELLCEPT® and Novartis under the brand name MYFORTIC®; azathioprine is currently available from Glaxo Smith Kline under the brand name IMURAN®; and antibodies are currently available from Ortho Biotech under the brand name ORTHOCLONE®, Novartis under the brand name SIMULECT® (basiliximab) and Roche under the brand name ZENAPAX® (daclizumab).

In one embodiment, compound I, or a pharmaceutically acceptable salt form thereof, is administered either in combination or adjunctively with an ophthalmic formulation of a drug such as an antihistamine, an antibiotic, an anti-inflammatory, an antiviral or a glaucoma medication. Such combination preparations are particularly useful to treating cases of DLE that primarily affect the skin around the eye (such as the eyelids), and may be administered to or around the eye, for example in drops or ointments. When preparing these combination formulations, compound I, including the pharmaceutically acceptable salt form thereof, may be combined with ophthalmic antibiotics (such as sulfacetamide, erythromycin, gentamicin, tobramycin, ciprofloxacin or ofloxacin); ophthalmic corticosteroids (such as prednisolone, fluorometholone or dexamethasone; ophthalmic non-steroidal anti-inflammatories (such as ibuprofen, diclofenac, ketorolac or flurbiprofen); ophthalmic antihistamines (such as livostin, patanol, cromolyn, alomide, or pheniramine); ophthalmic antiviral eye medications (such as triflurthymidine, adenine, arabinoside or idoxuridine); ophthalmic glaucoma medications (for example beta-blockers such as timolol, metipranolol, carteolol, betaxolol or levobunolol); ophthalmic prostaglandin analogues (such as latanoprost); ophthalmic cholinergic agonists (such as pilocarpine or carbachol); ophthalmic alpha agonists such as bromonidine or iopidine; ophthalmic carbonic anhydrase inhibitors (such as dorzolamide); and ophthalmic adenergic agonists (such as epinephrine or dipivefrin).

IV. EXAMPLES

Instruments, Materials, and Analysis

High Performance Liquid Chromatography (HPLC):

An HPLC system with gradient elution, UV detector and data acquisition was used. Column: Waters SymmetryShield RP 18, 3.5 μm, 4.6×150 mm.

Differential Scanning Calorimetry (DSC):

A sample of 2-6 mg is placed in an aluminum pan and crimped with an aluminum lid. The sample is equilibrated at 25° C. and heated to 285° C. or 300° C. at a heating rate of 10° C./min under a nitrogen stream.

Thermogravimetric Analysis (TGA):

A sample of 2-6 mg is placed in an aluminum pan and the pan is left open. The sample is heated from ambient temperature to 175° C. or 300° C. at a heating rate of 10° C./min under a nitrogen stream.

X-Ray Powder Diffraction (XRPD):

XRPD data are collected from 3° to 40° 20 with steps of 0.02° at a scan speed of 1.0°/min. The powder samples are prepared using a top loading sample holder and illuminated with Cu Kα radiation (λ=1.54056 Å) at 30 kV and 15 mA.

Polarizing Light Microscope (PLM):

Samples are dispensed on glass slide, covered with cover glass, and analyzed by an optical microscope at 200-400 times magnification in bright fields.

Karl Fischer Coulometer:

A sample of 5-20 mg is placed in a plastic spatula. The spatula is inserted into the tank such that the entire sample is submerged in the media. The water content is measured at ambience.

Preparation of Semi-Solid Samples:

Excipients and active pharmaceutical ingredient (API) are added to a glass container, and heated and/or sonicated at 65° C. to 70° C. to dissolve API completely. The sample is then cooled to room temperature.

In Vitro Franz Diffusion Assay:

The receptor compartment is filled with phosphate-buffered saline/propylene glycol/ethanol/Polysorbate80 45/40/10/5 (% v/v). The receptor media is stirred by a magnetic stir-bar. About 500 mg of topical formulation sample is weighed and added to the donor compartment. The two compartments are separated by a cellulose acetate membrane filter (0.45 μm, diameter 25 mm, ref #10 404 006, lot #EY0302-1, from Whatman), which has been soaked in the media for 24 hours. The assay is carried out at room temperature and lasts six hours. Approximately 0.2 mL of receptor media is collected every hour, and the receptor compartment is immediately refilled with fresh media. The API concentration in the receptor is analyzed by HPLC.

Water Activity:

Water activity is measured by a Rotronic probe (model #AW-DIO, S/N #129237). A sample of 1 g is placed in the sample cup. The probe is put immediately on the sample cup in order to avoid humidity exchange with the ambient. Measurements are not taken until the humidity and temperature values are stable (no change of both values for 1-2 minutes).

Viscosity:

Viscosity is measured by a Hydramotion Viscolite portable viscometer (model #VL700-T15, S/N #L1004-1090). The sensor is immersed into the sample. If the sample is at a different temperature than the sensor, sufficient time is allowed for complete temperature equilibration before reading.

Example 1

Preliminary Stability Study

A solution (10 mg/g compound I in DMI/PG/PEG400/EtOH 20/40/10/30) and a semi-solid formulation (10 mg/g in DMI/PG/PEG400/PEG8000/Tefose® 63 20/40/10/25/5) of the compound I besylate salt were prepared. After one month during the stability study of the semi-solid formulation at 40° C./75% RH, the purity of 1% active was found to be 98.5% compared with 99.8% at study initiation (TO), and the samples turned to pale yellow compared with off-white at TO, suggesting the API might have been oxidized. The follow-on evaluation of a solution formulation with antioxidants under accelerated stressed condition at 60° C./80% RH for a week revealed that the label strength was about 100% with BHT, BHA, and vitamin E, but was decreased to 90% with vitamin C. Among these antioxidants, only BHT-containing samples showed no color change.

Example 2

Solubility Studies

The solubility studies of compound I were carried out and the results are shown in Table 1. The solubility of compound I free base in water is only 2 μg/mL. PEG400 and glycofurol were found to be excellent solvents for compound I free base with solubility greater than 200 mg/mL, while solubility of compound I besylate in PEG400 was only 48 mg/mL. Accordingly, the free base was utilized for the formulation development of compound I.

TABLE 1

Solubility Studies of Compound I (including Free Base, HCl, and besylate)

| Solvent | Solubility (mg/mL) |
|---|---|
| Water | 0.002 [a] |
| EtOH | 3.2 [a] |
| PEG400 | 292 [a] |
| DMI | 124 [a] |
| Glycofurol | >205 [b] |
| Glycofurol/water 9/1 w/w | >202 [b] |
| Glycofurol/water 8/2 | <205 [b] |

TABLE 1-continued

Solubility Studies of Compound I (including Free Base, HCl, and besylate)

| Solvent | Solubility (mg/mL) |
|---|---|
| Castor Oil | 7.4 [c] |
| Miglyol 812N | 2.3 [c] |
| PEG400 | 129 [c] |
| PG | 27 [c] |
| 4% $H_2O$-96% THF | 77 [c] |
| 12% $H_2O$-88% THF | 202 [c] |
| 16% $H_2O$-84% THF | 163 [c] |
| 20% $H_2O$-80% THF | 133 [c] |
| 5% THF-95% PEG400 | 117 [c] |
| 10% THF-90% PEG400 | 129 [c] |
| 90% THF-10% PEG400 | 75 [c] |
| 95% THF-5% PEG400 | 70 [c] |
| 20% EtOH-80% PEG400 | 126 [c] |
| 50% EtOH-50% PEG400 | 136 [c] |
| PEG400 | 48 [d] |
| PG | 15 [d] |
| EtOH | 0.3 [e] |
| IPA | 0.037 [e] |
| PEG400 | 2.6 [e] |
| PG | 5.2 [e] |
| 40% TPGS/60% PEG400 | 1.7 [e] |
| Oleyl alcohol | 0.2 [e] |
| DMI | 0.4 [e] |
| Isopropyl Myristate | 0.005 [e] |
| Polyoxyglyceride (Labrasol) | 1.8 [e] |
| Propylene Glycol Laurate (Lauroglycol FCC) | 0.02 [e] |
| Polyoxyglyceride (Labrafil M1944 CS) | 0.07 [e] |
| Triglyceride | 0.02 [e] |
| Diethylene glycol monoethyl ether (transcutol P) | 0.9 [e] |
| Propylene Glycol Monocaprylate (Capryol 90) | 0.07 [e] |

[a] determined at 25° C. with compound I free base
[b] Compound I free base
[c] Compound I free base
[d] Compound I besylate salt
[e] Compound I HCl

Example 3

Formulation Development

Topical formulations of compound I were developed based on the following considerations: 1) the highest possible concentration of compound I for clinical use, 2) solubility of compound I in the formulation matrix for skin penetration, 3) adequate physical and chemical stability to provide a product with an acceptable shelf life for clinical studies and eventual commercialization, 4) good penetration for compound I such that a sufficient amount of compound I can be delivered into the skin, 5) suitability for commercial-scale production, and/or 6) an aesthetically pleasing feel and easy spreadability on the skin. A target product profile included the following characteristics: a semi-solid solution suitable for storage in a conventional plastic tube for multiple doses, e.g., 5-50 mL; stable when stored at room temperature (15-25° C.); pH 7±0.5; bacterial and mold resistant; no irritation, burning, or stinging; as isotonic as possible, lotion-like; sufficient shelf life, i.e., at least 2 years at room temperature.

Table 2 is a list of the excipients used in the formulations and their functionality.

TABLE 2

List of excipients and their functions

| Excipient | Function |
|---|---|
| PEG400, Glycofurol | Solvent |
| PEG8000, PEG4500, PEG3350 | Topical Base |
| Tefose ® 63, Span ®, Myrj ®, TPGS | Surfactant |
| DMI, PG | Penetration enhancer |
| $H_2O$ | Emollient |
| BHT | Antioxidant |
| Caramel | Color Additive |

Formulations with PEG8000/PEG3350/PEG4500 (Table 3):

The formulation with PEG8000 was placed at 40° C./75% RH and was found very hard and dry after one month. PEG8000 was replaced with lower melting point PEG3350 and PEG4500. F#2 with 25% PEG3350 was not clear at 65° C. and was free-flowing liquid at room temperature, indicating that the viscosity was too low. Replacing PEG3350 with PEG4500 and keeping the other excipients and their amounts the same led to F#3, which was no longer a free-flowing liquid. Reducing water to 4% in F#4 resulted in a grainy and dry semisolid. Increasing water to 6% yielded grainy and dry formulations (F#7 and F#10). Increasing water to 8% (F#8) resulted in a less grainy and less dry semisolid.

TABLE 3

Compositions and characterization of formulations with PEG8000/PEG3350/PEG4500 as base

| F# | Cpd I mg/g | DMI % w/w | PG % w/w | PEG400 % w/w | PEG3350 % w/w | PEG4500 % w/w | PEG8000 % w/w | Tefose63 % w/w | BHT % w/w | $H_2O$ % w/w | Total | Appearance |
|---|---|---|---|---|---|---|---|---|---|---|---|---|
| 1 | 40 | 15 | 10 | 34 | | | 25 | 5 | 1 | 10 | 100 | Clear at 65 C. semisolid |
| 2 | 20 | 15 | 10 | 34 | 25 | | | 5 | 1 | 10 | 100 | Not clear at 65 C., liquid-like, free-flowing |
| 3 | 20 | 15 | 10 | 34 | | 25 | | 5 | 1 | 10 | 100 | Not clear at 65 C., liquid-like, not free-flowing |
| 4 | 20 | 15 | 10 | 34 | | 31 | | 5 | 1 | 4 | 100 | Not clear at 65 C., dry, grainy semisolid |
| 5 | 20 | 15 | 16 | 34 | | 25 | | 5 | 1 | 4 | 100 | Almost clear at 65 C., dry, grainy semisolid |
| 6 | 20 | 15 | 10 | 40 | | 25 | | 5 | 1 | 4 | 100 | Not clear at 65 C., dry, grainy semisolid |
| 7 | 20 | 15 | 14 | 34 | | 25 | | 5 | 1 | 6 | 100 | Clear at 65 C. grainy, dry semisolid |
| 8 | 20 | 15 | 12 | 34 | | 25 | | 5 | 1 | 8 | 100 | Clear at 65 C. less grainy, less dry semisolid |
| 9 | 20 | 15 | 34 | 14 | | 25 | | 5 | 1 | 6 | 100 | Not clear at 65 C., free-flowing, wet, soft |
| 10 | 20 | 15 | 24 | 24 | | 25 | | 5 | 1 | 6 | 100 | Almost clear at 65 C., grainy, semisolid |

Formulations with Water (Table 4):

Emollience is one of the key attributes of topical formulation for skin. Water was introduced to the formulation to lower the viscosity of the product and compensate any possible water loss from the skin due to the use of hygroscopic excipients such as PEG400 and higher PEGs in the formulations. Water also happened to lend good texture and feel to the formulations. F#1, which contained no water, was clear at 65° C., indicating one phase was achieved for this complex 5-component mixture. In particular disclosed embodiments when water was introduced as low as 4% to the formulation, a one-phase solution at 65° C. was not obtained (F#3, F#4, and F#5). Increasing water to 10% and keeping PEG400 at 10% (F#6) created a solubility issue to maintain 20 mg/mL solution of compound I. Increasing PEG400 to 34% (F#7) and keeping water at 10% resulted in a one-phase solution at 65° C. due to high solubility of compound I in PEG400 (292 mg/mL).

TABLE 4

Compositions and characterization of formulations with water added

| F# | Cpd I mg/g | DMI % w/w | PG % w/w | PEG400 % w/w | PEG8000 % w/w | Tefose63 % w/w | BHT % w/w | $H_2O$ % w/w | Total | Clear at 65° C. | Appearance |
|---|---|---|---|---|---|---|---|---|---|---|---|
| 1 | 20 | 15 | 40 | 14 | 25 | 5 | 1 | | 100 | Yes | Off-white semisolid |
| 2 | 40 | 15 | 40 | 14 | 25 | 5 | | | 99 | No | Light yellow semisolid |
| 3 | 20 | 15 | 40 | 10 | 25 | 5 | 1 | 4 | 100 | No | Off-white semisolid |
| 4 | 20 | 15 | 40.9 | 10 | 25 | 5 | 0.1 | 4 | 100 | No | Off-white semisolid |
| 5 | 20 | 15 | 40 | 10 | 25 | 5 | | 4 | 99 | No (only after Tefose63) | Light yellow semisolid |
| 6 | 20 | | 34 | 10 | | | | 10 | 54 | No (Cpd. I precipitated) | Off-white semisolid |
| 7 | 40 | 15 | 10 | 34 | 25 | 5 | 1 | 10 | 100 | Yes | Off-white semisolid |

Replacement of Tefose® 63 with Myrj® 59 (Table 5):

Tefose® 63 is a mixture of PEG-6 stearate and ethylene glycol palmitostearate. It is a non-ionic oil-in-water emulsifier used to develop stable emulsions with high viscosity, and is widely used for mucosal application due to its light texture, excellent spreadability and softness. When water was added to the formulation, the immiscibility of water and Tefose® 63 posed potential physical stability issues: the formulation was no longer a one-phase system. Span families (Span® 20, Span® 40, Span® 80), Myrj® 45 and Myrj® 59 were tested, and only Myrj® 59 (F#6) yielded a one-phase solution at elevated temperature. Replacing Tefose® 63 with Myrj® 59 (F#10 over F#9) also increased the flux value of the formulation to 541 from 266, an indication of enhanced penetration.

Removal of PG (Table 6):

Removal PG from the formulation matrix was evaluated to make the formulation simpler. Initially, PG was selected because it is a well-known penetration enhancer. Removing PG in Tefose® 63-based formulations (F#A to F#B resulted in a small decrease in flux from 300 to 266. Among MYRJ59-based formulations, removal of PG produced a small increase from 458 to 583 in flux (F#C to F#D). This indicated that the contribution of PG to penetration for these formulations was not significant. Increasing PEG400 from 43% to 48% (F#4 to #5) to compensate for PG removal resulted in a less grainy and smoother formulation.

TABLE 5

Compositions and characterization of formulations with Tefose63 replaced by Myrj59

| F# | Cpd I mg/g | DMI % w/w | PG % w/w | PEG400 % w/w | PEG4500 % w/w | Surfactant % w/w | BHT % w/w | $H_2O$ % w/w | Total | Flux | Appearance |
|---|---|---|---|---|---|---|---|---|---|---|---|
| 1 | 20 | 15 | 10 | 34 | 25 | Tefose63 5 | 1 | 10 | 100 | | Not clear at 65 C. only after Tefose63, liquid-like, not free-flowing |
| 2 | 20 | 15 | 10 | 34 | 25 | Myrj45 5 | 1 | 10 | 100 | | Not clear at 65 C. only after Myrj45, semisolid |
| 3 | 20 | 15 | 10 | 34 | 25 | Span40 5 | 1 | 10 | 100 | | Not clear at 65 C. only after Span 40, semisolid |
| 4 | | 15 | 12 | 30 | 30 | Span20 5 | 1 | 8 | 100 | | Not clear at 65 C. only after Span20, semisolid |
| 5 | | 15 | 12 | 30 | 30 | Span80 5 | 1 | 8 | 100 | | Not clear at 65 C. only after Span80, semisolid |
| 6 | 20 | 15 | 10 | 34 | 25 | Myrj59 5 | 1 | 10 | 100 | | Clear at 65 C., semisolid, not grainy, soft, spreadable |
| 7 | 20 | 15 | 12 | 34 | 25 | Tefose63 5 | 1 | 8 | 100 | | Clear at 65 C., semisolid, a little grainy, spreadable |
| 8 | 20 | 15 | 12 | 32 | 27 | Tefose63 5 | 1 | 8 | 100 | | Clear at 65 C., semisolid, a little grainy, not dry, not wet, spreadable |
| 9 | 20 | 15 | | Glycofurol 39 | 34 | Tefose63 5 | 1 | 6 | 100 | 266 | Clear at 65 C., semisolid, not grainy, not dry, not loose, spreadable |
| 10 | 20 | 15 | | Glycofurol 39 | 34 | Myrj59 5 | 1 | 6 | 100 | 541 | Clear at 65 C., semisolid, not grainy, smooth, not dry, not wet, spreadable |

TABLE 6

Compositions and characterization of formulations for evaluation of the role of PG

| F# | Cpd I mg/g | DMI % w/w | PG % w/w | PEG400 % w/w | PEG4500 % w/w | Surfactant % w/w | BHT % w/w | $H_2O$ % w/w | Total | Flux | Appearance |
|---|---|---|---|---|---|---|---|---|---|---|---|
| A | 20 | 15 | 14 | Glycofurol 24 | 35 | Tefose63 5 | 1 | 6 | 100 | 300 | Clear at 65 C., semisolid, not grainy, not wet, spreadable |
| B | 20 | 15 | | Glycofurol 39 | 34 | Tefose63 5 | 1 | 6 | 100 | 266 | Clear at 65 C., semisolid, not grainy, not dry, not loose, spreadable |
| C | 20 | 15 | 10 | 34 | 25 | Myrj59 5 | 1 | 10 | 100 | 458 | Clear at 65 C., semisolid, not grainy, soft |
| 4 | | 15 | | 43 | 30 | Myrj59 5 | 1 | 6 | 100 | | Clear at 65 C., semisolid, a little grainy |
| 5 | | 15 | | 48 | 25 | Myrj59 5 | 1 | 6 | 100 | | Clear at 65 C., semisolid, smooth, soft, not grainy, not wet |
| D | 20 | 15 | | 48 | 25 | Myrj59 5 | 1 | 6 | 100 | 583 | Clear at 65 C., semisolid, not grainy, not wet, soft, smooth |
| 7 | 20 | 15 | | 48 | 25 | TPGS 5 | 1 | 6 | 100 | 382 | Clear at 65 C., semisolid, not grainy, uniform |

Evaluation of Penetration Enhancers (Table 7):

Out of 18 formulations in Table 7 for placebo and actives, 5 actives were selected for in vitro permeability assay after passing the evaluation of cosmetic feel and physical appearance. Reducing DMI from 15% to 10% (F#14 to #16) saw a small decrease of flux from 266 to 204. Replacing Tefose® 63 in F#16 with Myrj®59 in F#18 or TPGS in F#11 yielded improved flux of 541 and 484 respectively compared with 266. The combinations of glycofurol with either Myrj® 59 or TPGS provided enhanced penetration.

TABLE 7

Compositions and characterization of formulations: optimization of penetration enhancers

| F# | Cpd I mg/g | DMI % w/w | PG % w/w | Glycofurol % w/w | PEG4500 % w/w | Surfactant % w/w | BHT % w/w | $H_2O$ % w/w | Total | Flux | Appearance |
|---|---|---|---|---|---|---|---|---|---|---|---|
| 1 | 20 | 15 | 12 | 29 | 30 | Tefose63 5 | 1 | 8 | 100 | | Clear at 65 C., loose, free-flowing, fluid-like |
| 2 | 20 | 15 | 12 | 24 | 35 | Tefose63 5 | 1 | 8 | 100 | | Clear at 65 C., semisolid, not grainy, spreadable |
| 3 | 20 | 15 | 12 | 24 | 35 | Cetyl Alcohol 5 | 1 | 8 | 100 | | Clear at 65 C., semisolid, not homogeneous, grainy |
| 4 | 20 | 15 | 12 | 24 | 35 | TPGS 5 | 1 | 8 | 100 | | Clear at 65 C., semisolid, homogeneous, grainy, spreadable |
| 5 | 20 | 15 | 12 | 24 | 39 | Tefose63 5 | 1 | 4 | 100 | | Almost clear at 65 C., semisolid, dry, grainy, spreadable |
| 6 | 20 | 15 | 14 | 24 | 35 | Tefose63 5 | 1 | 6 | 100 | 300 | Clear at 65 C., semisolid, not grainy, not wet, spreadable |
| 7 | | 15 | | 31 | 42 | Tefose63 5 | 1 | 6 | 100 | | Almost clear at 65 C., semisolid, not homogeneous, not grainy, spreadable |
| 8 | | 15 | | 28 | 45 | Tefose63 5 | 1 | 6 | 100 | | Almost clear at 65 C., semisolid, dry, grainy |
| 9 | | 15 | | 34 | 39 | Tefose63 5 | 1 | 6 | 100 | | Almost clear at 65 C., semisolid, not homogeneous, spreadable |
| 10 | | 15 | | 39 | 34 | Tefose63 5 | 1 | 6 | 100 | | Clear at 65 C., semisolid, not grainy, not wet, not grainy, spreadable |
| 11 | 20 | 15 | | 39 | 34 | TPGS 5 | 1 | 6 | 100 | 484 | Clear at 65 C., semisolid, not grainy, spreadable, not dry |
| 12 | | 15 | | 39 | 34 | Myrj59 5 | 1 | 6 | 100 | | Clear at 65 C., semisolid, not grainy, spreadable, not wet |
| 13 | | 15 | | 42 | 36 | | 1 | 6 | 100 | | Clear at 65 C., semisolid, not grainy, not dry, not wet, spreadable |

TABLE 7-continued

Compositions and characterization of formulations: optimization of penetration enhancers

| F# | Cpd I mg/g | DMI % w/w | PG % w/w | Glycofurol % w/w | PEG4500 % w/w | Surfactant % w/w | BHT % w/w | $H_2O$ % w/w | Total | Flux | Appearance |
|---|---|---|---|---|---|---|---|---|---|---|---|
| 14 | 20 | 15 | | 39 | 34 | Tefose635 | 1 | 6 | 100 | 266 | Clear at 65 C., semisolid, not grainy, not dry, not loose, spreadable |
| 15 | 20 | 15 | 12 | 24 | 39 | Tefose635 | 1 | 4 | 100 | | Almost clear at 65 C., semisolid |
| 16 | 20 | 10 | | 44 | 34 | Tefose635 | 1 | 6 | 100 | 204 | Blurry at 65 C., not grainy, not dry, not wet, spreadable |
| 17 | 20 | 5 | | 49 | 34 | Tefose635 | 1 | 6 | 100 | | Blurry at 65 C., semisolid, uniform, not grainy, not dry, not wet |
| 18 | 20 | 15 | | 39 | 34 | Myrj595 | 1 | 6 | 100 | 541 | Clear at 65 C., semisolid, not grainy, smooth, not wet, not dry, spreadable |

Example 4

Clinical Formulation

Based on the formulation development work above, one type of formulation was selected as the prototype clinical formulation. PEG400 was selected over glycofurol due to its much wider use and ease in purchasing the GMP quality of PEG400; Myrj® 59 was selected over TPGS due to its wider use in the topical route. Further evaluation to obtain the optimal physical appearance by varying the ratio of PEG400/PEG4500/$H_2O$ was carried out and the results are listed in Tables 8 to 10. To lower the viscosity and increase the emollience of the ointment, water was added up to 14% (Table 8, F#1). With 2% compound I, the formulation was uniform, but too soft. The solubility study showed that a compound I concentration of 120 mg/g can be obtained at 45° C. in a formulation containing 14% water, 45% PEG400, and 20% PEG4500. Therefore, it was projected that toxicological formulations with 14% water would be able to contain 10% compound I without precipitation. Indeed, toxicological formulation prototypes at 6%, 8%, and 10% compound I were all clear at 65° C. during preparation (Table 8, F#3, F#2, and F#1, respectively). However, these three formulations never solidified at room temperature.

Reducing water to 10%, increasing PEG4500 to 20%, and reducing PEG400 to 39% afforded semi-solid formulation E with acceptable physical appearance and stability at 10% compound I (Table 9).

TABLE 8

Compositions and characterization of formulations containing 14% $H_2O$

| F# | Cpd I mg/g | DMI % w/w | PEG400 % w/w | PEG4500 % w/w | Myrj59 % w/w | BHT % w/w | H2O % w/w | Total | Appearance |
|---|---|---|---|---|---|---|---|---|---|
| 1 | 20 | 15 | 45 | 20 | 5 | 1 | 14 | 100 | Clear at 65 C., semisolid at RT, uniform, slowly free-flowing |
| 2 | 100 | 15 | 45 | 10 | 5 | 1 | 14 | 100 | Clear at 65 C.; Cloudy, yellow solution at RT (never solidified) |
| 3 | 80 | 15 | 45 | 12 | 5 | 1 | 14 | 100 | Clear at 65 C.; Cloudy, yellow solution at RT (never solidified) |
| 4 | 60 | 15 | 45 | 14 | 5 | 1 | 14 | 100 | Clear at 65 C.; Cloudy, yellow solution at RT (never solidified) |

TABLE 9

Compositions and characterization of prototype formulations for toxicological uses

| F# | Cpd I mg/g | DMI % w/w | PEG400 % w/w | PEG4500 % w/w | Myrj59 % w/w | BHT % w/w | $H_2O$ % w/w | Total | Appearance |
|---|---|---|---|---|---|---|---|---|---|
| E | 100 | 15 | 39 | 20 | 5 | 1 | 10 | 100 | Clear at 65 C.; Solidified fastest among the three; No Cpd I crystal in PLM |
| 1 | 100 | 15 | 42 | 17 | 5 | 1 | 10 | 100 | Clear at 65 C.; Solidified slowly after 2 days at RT |
| 2 | 100 | 15 | 44 | 15 | 5 | 1 | 10 | 100 | Clear at 65 C.; Solidified slowly |

Based on formulation E, prototype clinical formulations at 0.2%, 2%, and 4% strengths were developed for a stability study. Keeping water at 10% and PEG4500 at 20% and compensating the change in compound I with PEG400 yielded a formulation prototype for compound I with 4% strength (Table 11, F#1). The formulation was clear at 65° C., was soft but not loose, and was not grainy semi-solid at room temperature. Using the same approach, formulation prototypes at 0.2%, 1% (F#F), 2%, 3% (F#G), 4%, and 6% (F#H) compound I were developed (Table 10). All of them were one-phase solutions at 65° C. and had acceptable physical appearance and texture at room temperature. Formulations at 0.2%, 2%, and 4% compound I were placed in a long-term stability study.

TABLE 10

Compositions and characterization of prototype formulations

| F# | Cpd I mg/g | DMI % w/w | PEG400 % w/w | PEG4500 % w/w | Myrj59 % w/w | BHT % w/w | $H_2O$ % w/w | Total (including Cpd I) | Appearance |
|---|---|---|---|---|---|---|---|---|---|
| 1 | 40 | 15 | 45 | 20 | 5 | 1 | 10 | 100 | Clear at 65 C.; Filled in tubes as liquid; Squeezed out after 2 days at RT: soft, not grainy, not loose |
| 2 | 20 | 15 | 47 | 20 | 5 | 1 | 10 | 100 | Clear at 65 C.; Stirred while cooling; soft, smooth, not grainy, homogeneous |
| 3 | 2 | 15 | 48.8 | 20 | 5 | 1 | 10 | 100 | Clear at 65 C.; Stirred while cooling; soft, smooth, not grainy, homogeneous |
| 4 | | 15 | 49 | 20 | 5 | 1 | 10 | 100 | Clear at 65 C.; Stirred while cooling; soft, smooth, not grainy, homogeneous |
| F | 10 | 15 | 48 | 20 | 5 | 1 | 10 | 100 | Clear at 65 C.; Stirred while cooling; soft, uniform |
| G | 30 | 15 | 46 | 20 | 5 | 1 | 10 | 100 | Clear at 65 C.; Stirred while cooling; soft, uniform |
| H | 60 | 15 | 43 | 20 | 5 | 1 | 10 | 100 | Clear at 65 C.; Stirred while cooling; soft, uniform, homogeneous |

To minimize the differences in appearance among the actives and placebo and facilitate the double blinding in clinical studies, a color additive was sought and evaluated. Caramel is a widely used color additive in drug industry and is one of a few color additives exempt from batch certification. In the FDA's inactive ingredients list, caramel is used up to 0.26% for topical applications.

Several experiments were performed to study the effectiveness of masking color difference using 0.05% to 0.2% caramel (Table 11). Formulations I and J with 0.2% caramel appeared as a brown semi-solid. Formulations K and L with 0.1% caramel appeared as a faint brown semi-solid. Formulations M and N with 0.05% caramel appeared as a beige semi-solid. None of them had the caramel smell. It was observed that 0.1% or 0.05% caramel effectively masked the color difference between placebo and 6% active. The accelerated stress study of formulations with caramel at 60° C. for 3 days revealed that no new impurities were found by HPLC.

TABLE 11

Compositions and characterization of formulations containing caramel as color additive

| F# | Caramel % w/w | Cpd I mg/g | DMI % w/w | PEG400 % w/w | PEG4500 % w/w | Myrj59 % w/w | BHT % w/w | $H_2O$ % w/w | Total | Appearance |
|---|---|---|---|---|---|---|---|---|---|---|
| I | 0.2 | 0 | 15 | 49 | 20 | 5 | 1 | 10 | 100.2 | Hazy, dark brown at 65 C.; semisolid, homogeneous, smooth, spreadable, soft, brown but lighter than 1682-127-02 |
| J | 0.2 | 60 | 15 | 43 | 20 | 5 | 1 | 10 | 100.2 | Hazy, dark brown at 65 C.; semisolid, homogeneous, smooth, spreadable, soft, brown but darker than 1682-127-01 |
| K | 0.1 | 0 | 15 | 49 | 20 | 5 | 1 | 10 | 100.1 | Clear, dark brown at 65 C.; semisolid, smooth, homogeneous, soft, spreadable, light faint brown, lighter than 1682-128-05 on white paper |

TABLE 11-continued

Compositions and characterization of formulations containing caramel as color additive

| F# | Caramel % w/w | Cpd I mg/g | DMI % w/w | PEG400 % w/w | PEG4500 % w/w | Myrj59 % w/w | BHT % w/w | $H_2O$ % w/w | Total | Appearance |
|---|---|---|---|---|---|---|---|---|---|---|
| L | 0.1 | 60 | 15 | 43 | 20 | 5 | 1 | 10 | 100.1 | Clear, dark brown at 65 C.; semisolid, smooth, homogeneous, soft, spreadable, light brown/beige, darker than 1682-128-03 on white paper |
| M | 0.05 | 0 | 15 | 49 | 20 | 5 | 1 | 10 | 100.05 | Clear, brown at 65 C.; semisolid, smooth, homogeneous, spreadable, beige/sandy, slightly lighter than 1682-128-06 on white paper |
| N | 0.05 | 60 | 15 | 43 | 20 | 5 | 1 | 10 | 100.05 | Clear, brown at 65 C.; semisolid, smooth, homogeneous, spreadable, beige/sandy, slightly darker than 1682-128-04 on white paper |

Example 5

Assay for Ramos B-Cell Line Stimulated with IL-4

One means of assaying for JAK inhibition is detection of the effect of compound I on the upregulation of downstream gene products. In the Ramos/IL4 assay, B-cells are stimulated with the cytokine Interleukin-4 (IL-4) leading to the activation of the JAK/Stat pathway through phosphorylation of the JAK family kinases, JAK1 and JAK3, which in turn phosphorylate and activate the transcription factor Stat-6. One of the genes upregulated by activated Stat-6 is the low affinity IgE receptor, CD23. To study the effect of inhibitors (for example, the 2,4-substituted pyrimidinediamine compounds described herein) on the JAK1 and JAK3 kinases, human Ramos B cells are stimulated with human IL-4. Twenty to 24 hours post stimulation, cells are stained for upregulation of CD23 and analyzed using flow cytometry (FACS). A reduction of the amount of CD23 present compared to control conditions indicates the test compound actively inhibits the JAK kinase pathway. An exemplary assay of this type is described in greater detail below.

B-cells stimulated with cytokine Interleukin-4 (IL-4) activate the JAK/Stat pathway through phosphorylation of the JAK family kinases, JAK-1 and JAK-3, which in turn phosphorylate and activate the transcription factor Stat-6. One of the genes upregulated by activated Stat-6 is the low affinity IgE receptor, CD23. To study the effect of inhibitors on the JAK family kinases, human Ramos B cells are stimulated with human IL-4.

The Ramos B-cell line was acquired from ATCC (ATCC Catalog No. CRL-1596). The cells were cultured in RPMI 1640 (Cellgro, MediaTech, Inc., Herndon, Va., Cat No. 10-040-CM) with 10% fetal bovine serum (FBS), heat inactivated (JRH Biosciences, Inc., Lenexa, Kans., Cat No. 12106-500M) according to ATCC propagation protocol. Cells were maintained at a density of $3.5\times10^5$. The day before the experiment, Ramos B-cells were diluted to $3.5\times10^5$ cells/mL to ensure that they were in a logarithmic growth phase.

Cells were spun down and suspended in RPMI with 5% serum. $5\times10^4$ cells were used per point in a 96-well tissue culture plate. Cells were pre-incubated with compound I or DMSO (Sigma-Aldrich, St. Louis, Mo., Cat No. D2650) vehicle control for 1 hour in a 37 C incubator. Cells were then stimulated with IL-4 (Peprotech Inc., Rocky Hill, N.J., Cat No. 200-04) for a final concentration of 50 units/mL for 20-24 hours. Cells were then spun down and stained with anti-CD23-PE (BD Pharmingen, San Diego, Calif., Cat No. 555711) and analyzed by FACS. Detection was performed using a BD LSR I System Flow Cytometer, purchased from Becton Dickinson Biosciences of San Jose, Calif. Compound I provided an $IC_{50}$ of 0.056 nM.

Example 6

Primary Human T-Cell Proliferation Assay Stimulated with IL-2

The JAK activity of compound I may further be characterized by assaying the effect of compound I on the proliferative response of primary human T-cells. In this assay, primary human T-cells derived from peripheral blood and pre-activated through stimulation of the T-cell receptor and CD28, proliferate in culture in response to the cytokine Interleukin-2 (IL-2). This proliferative response is dependent on the activation of JAK1 and JAK3 tyrosine kinases, which phosphorylate and activate the transcription factor Stat-5. The primary human T-cells are incubated with compound I in the presence of IL-2 for 72 hours and at the assay endpoint intracellular ATP concentrations are measured to assess cell viability. A reduction in cell proliferation compared to control conditions is indicative of inhibition of the JAK kinase pathway. An exemplary assay of this type is described in greater detail below.

Primary human T-cells derived from peripheral blood and pre-activated through stimulation of the T-cell receptor and CD28, proliferate in vitro in response to the cytokine Interleukin-2 (IL-2). This proliferative response is dependent on the activation of JAK-1 and JAK-3 tyrosine kinases, which phosphorylate and activate the transcription factor Stat-5.

Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 min at 4° C. at 1750 rpm. The lymphocytes at the serum: ficoll interface were recovered and washed twice with 5 volumes of PBS. The cells were resuspended in Yssel's medium (Gemini Bio-products, Woodland, Calif., Catalog #400-103) containing 40 U/mL recombinant IL2 (R and D Systems, Minneapolis, Minn., Catalog #202-IL (20 g)) and seeded into a flask pre-coated with 1 μg/mL anti-CD3 (BD Pharmingen, San Diego, Calif., Catalog #555336) and 5 μg/mL anti-CD28 (Immunotech, Beckman Coulter of Brea Calif., Catalog #IM1376). The primary T-cells were stimulated for 3-4 days, then transferred to a fresh flask and maintained in RPMI with 10% FBS and 40 U/mL IL-2.

Primary T-cells were washed twice with PBS to remove the IL-2 and resuspended in Yssel's medium at $2\times10^6$ cells/mL. 50 L of cell suspension containing 80 U/mL IL-2 was added to each well of a flat bottom 96 well black plate. For the unstimulated control, IL-2 was omitted from the last column on the plate. Compound I was serially diluted in dimethyl sulfoxide (DMSO, 99.7% pure, cell culture tested, Sigma-Aldrich, St. Louis, Mo., Catalog No. D2650) from 5 mM in 3-fold dilutions, and then diluted 1:250 in Yssel's medium. 50 μL of 2× compound was added per well in duplicate and the cells were allowed to proliferate for 72 hours at 37 C.

Proliferation was measured using CellTiter-Glo® Luminescent Cell Viability Assay (Promega), which determines the number of viable cells in culture based on quantitation of the ATP present, as an indicator of metabolically active cells. The substrate was thawed and allowed to come to room temperature. After mixing the Cell Titer-Glo® reagent and diluent together, 100 L was added to each well. The plates were mixed on an orbital shaker for two minutes to induce lysis and incubated at room temperature for an additional ten minutes to allow the signal to equilibrate. Detection was performed using a Wallac Victor2 1420 multilabel counter purchased from Perkin Elmer, Shelton, Conn. The $IC_{50}$ calculated based on the results of this assay was 0.181 nM.

Example 7

Cutaneous Lupus Mouse Model

This example describes the use of mouse models to screen for treatments for cutaneous lupus (such as DLE), including the selection of regimens for treatment, prevention and combination treatments. Animal models are used to test the disclosed compounds, as well as combination formulations, such as those described herein. In particular examples, topical formulations that contain compound I are applied to the skin of the animal and the therapeutic response is assessed. After the formulations are administered to the animal, the skin is examined for evidence of decreased number or severity of cutaneous lesions.

Although no single animal-based model has been found to ideally mimic DLE, the MRL/lpr mouse strain has been beneficial as a research tool. Transgenic or knock-out forms of these autoimmune mice have been used to explore manifestations of cutaneous lupus. In the MRL/lpr mouse, the lpr mutation results in an alternation in the Fes gene and a defect of apoptosis resulting in abnormal lymphocyte proliferation with abnormal function and auto-antibody production. These animals develop spontaneous lupus-like skin lesions that are common in early life and become progressively more severe as the mice age. Ghoreishi and Dutz, Lupus 19:1029-1035 (2010).

An alternative mouse model is the TCRα−/− mouse treated with fluorouracil and ultraviolet B light irradiation to induce cutaneous lupus lesions. Furukawa and Yoshimasu, Autoimmunity Reviews 4:345-350 (2005).

However, the presently preferred mouse model for demonstrating and testing the efficacy of the currently disclosed treatments is use of the lupus-prone $(NZBxNZW)F_1$ mice, as disclosed in Guiducci et al., Journal of Experimental Medicine 207:2931-2942 (2010), which is incorporated by reference. These lupus-prone mice develop chronic skin lesions resembling human chronic lupus erythematosus after tape stripping.

The lupus-prone $(NZBxNZW)F_1$ mice are available from The Jackson Laboratory, and may be used at 18-22 weeks of age. C57BL/6 and 129 mice are available as controls (for example from Charles River). The dorsal areas of the mice are shaved in a 3×3 cm area, and tape stripping is performed with 10 strokes of duct tape. The skin will show an increase in the number of PDCs and neutrophils, and the abundant cellular infiltrate is accompanied by increased expression of IFN-regulated and proinflammatory genes Approximately three weeks following tape stripping the mice have prominent epidermal hyperplasia with hyperkeratosis, keratin-filled craters or cysts, dermal fibrosclerosis and degenerative changes of the subcutaneous fat. These changes are similar to those seen in humans with chronic lupus erythematosus.

In the model, the mouse is exposed to the test agent, using different routes, dosages and regimens of administration. In particular examples, the pharmaceutical formulations disclosed herein are applied topically to the areas that have been or will be tape stripped. The formulation is administered one or more times at fixed intervals prior to or following tape stripping (for example, daily following tape stripping or following the appearance of the skin lesions). Drug response can be assessed by measuring such indicia of disease as the number, surface area or appearance of cutaneous lesions. Even if the number or surface area of lesions is not reduced, the severity of the lesions (such as levels of erythema) can be measured in assessing response to the test treatments. Histological analysis of skin specimens is also performed, and the specimens are graded from 1 to 3 based on the following criteria: (a) epidermis thickness; (b) degree of ulceration; (c) intraepithelial inflammation; (d) dermal inflammation; and (e) panniculus inflammation. Histological grading is assigned as follows: 0, normal skin architecture, few dermal leukocytes, and regular adnexa; 1: mild inflammation, slight epidermal hyperplasia, and signs of dermal fibroblast proliferation; 2: moderate inflammation, noticeable epidermal hyperplasia (two-to fourfold increase in epithelial thickness) with hyperkeratosis, significant leukocyte/neutrophil-granulocyte dermal infiltrate with few macrophages, moderate fibrosclerosis of the dermis, reduction in the number of adnexa, and slight degenerative changes of the hypodermic adipose tissue; and 3: severe inflammation, marked epihermal hyperplasia (more than fourfold increase in epithelial thickness) with hyperkeratosis, formation of keratin-filled craters and cysts, diffuse discontinuity of the epidermal layer (ulceration), extensive dermal infiltrate with abundant neutrophils and macrophages, pronounced dermal fibrosclerosis, vanishing of adnexa, and evident degenerative changes of the hypodermic adipose tissue. The different parameters are scored and summed to obtain a total disease score. Cellular infiltrates may be processed using flow cytometry.

Example 8

Methods of Treatment and Combination Formulations

Subjects to be treated with the disclosed formulations are selected based on a clinical presentation of cutaneous lupus erythematosus, such as DLE, ACLE, SCLE or DILE. This example specifically addresses the treatment of DLE, but a similar method of treatment can be used for other cutaneous forms of lupus, such as ACLE, SCLE or DILE. The disclosed compositions are generally applied topically to the DLE lesions on the skin, for example only to the DLE lesions on the skin, although they may also be applied more generally to the skin. Treatment may be continued for at least a week, month, or year, and in some subjects treatment may extend over multiple years, the duration of disease, or the lifetime of the subject.

In particular cases, subjects are selected for concomitant treatment with other pharmaceutical or non-pharmaceutical interventions, such as systemic PLAQUENIL® or topical corticosteroid. In other cases, compound I is administered with no other treatment for LE or DLE, such as systemic PLAQUENIL® or systemic or topical corticosteroid. In other embodiments, the method includes administering the treatment to a subject with DLE who does not have anti-DNA antibodies, for example anti-ds-DNA antibodies.

The subject is selected by making a diagnosis of a cutaneous lupus erythematosus, for example a chronic cutaneous lupus erythematosus, such as DLE. In this particular example, a subject is selected who does not have SLE (for example, by not having anti-ds DNA antibodies or systemic manifestations of SLE such as inflammation of the kidneys, lung, central nervous system, or any organ other than the skin or mucous membranes of the eyes, nose or mouth). In other examples, the subject only has skin manifestations of disease on the surface of the body, and not lesions of any other organ of the body. A therapeutically effective amount of the compound is provided in a topical formulation, and the formulation is applied directly to cutaneous lupus erythematosus lesions, such as scaling papules on the trunk and extensor surfaces of the extremities and/or scalp. The pharmaceutical formulation is applied to the lesions daily, for example 2-4 times per day for more than one day, for example at least one week. Topical application of the formulation to the lesions is continued until the lesions to which the formulation is applied regress or disappear, or their progression is delayed or stopped.

In other examples, the therapeutic compound is provided in an effective amount in a sunscreen formulation and is applied to the skin prior to exposure to ultraviolet radiation, to protect against exposure to ultraviolet radiation which is often a trigger for the eruption of cutaneous lupus lesions. The sunscreen formulation may contain, for example, an effective amount of PABA or zinc oxide to minimize skin exposure to ultraviolet radiation.

Combination therapies are also provided that combine compound I (which includes salts thereof) with another agent that treats the cutaneous lupus or another condition, such as a condition associated with the dry eyes. Combination formulations for the treatment of cutaneous lupus (such as DLE) include combination formulations that include a topical corticosteroid, such as a Group I, II, III, IV, V, VI or VII corticosteroid, for example any of the following:

Group I (Very Potent: Up to 600 Times Stronger than Hydrocortisone)

Clobetasol propionate 0.05% (Dermovate)
Betamethasone dipropionate 0.25% (Diprolene®)
Halobetasol proprionate 0.05% (Ultravate®)
Diflorasone diacetate 0.05% (Psorcon®)

Group II

Fluocinonide 0.05% (Lidex®)
Halcinonide 0.05% (Halog®)
Amcinonide 0.05% (Cyclocort®)
Desoximetasone 0.25% (Topicort®)

Group III

Triamcinolone acetonide 0.5% (Kenalog®, Aristocort cream)
Mometasone furoate 0.1% (Elocon® ointment)
Fluticasone propionate 0.005% (Cutivate®)
Betamethasone dipropionate 0.05% (Diprosone)

Group IV

Fluocinolone acetonide 0.01-0.2% (Synalar®, Synemol, Fluonid)
Hydrocortisone valerate 0.2% (Westcort®)
Hydrocortisone butyrate 0.1% (Locoid®)
Flurandrenolide 0.05% (Cordran®)
Triamcinolone acetonide 0.1% (Kenalog®, Aristocort A® ointment)
Mometasone furoate 0.1% (Elocon® cream, lotion)

Group V

Triamcinolone acetonide 0.1% (Kenalog®, Aristocor®t cream, lotion)
Fluticasone propionate 0.05% (Cutivate® cream)
Desonide 0.05% (Tridesilon, DesOwen® ointment)
Fluocinolone acetonide 0.025% (Synalar®, Synemol cream)
Hydrocortisone valerate 0.2% (Westcort® cream)

Group VI

Prednicarbate 0.05% (Aclovate® cream, ointment)
Triamcinolone acetonide 0.025% (Aristocort A® cream, Kenalog® lotion)
Fluocinolone acetonide 0.01% (Capex® shampoo, Dermasmooth)
Desonide 0.05% (DesOwen® cream, lotion)

Group VII

Hydrocortisone 2.5% (Hytone® cream, lotion, ointment)
Hydrocortisone 1% (many over-the-counter brands)

In some examples, the subject is diagnosed with a disorder in addition to cutaneous lupus, wherein the additional disorder is not caused by lupus erythematosus, or is not a manifestation of or associated with lupus erythematosus. For example, a subject with cutaneous lupus eyelid lesions may also be diagnosed with dry eyes and the combination therapy is administered to the subject. In one example, the subject is found to have a meibomitis that would be responsive to topical application of corticosteroids, such as a prednisolone acetate ophthalmic suspension 1%. Compound I (which includes salts thereof) is suspended in the prednisolone formulation and instilled in or applied to the eye 2 to 4 times a day. In other examples, if the dry eyes are associated with seasonal allergies or other inflammatory conditions, the eye drops are administered with or in a formulation that includes antihistamines (such as pheniramine, emedastine, or azelastine), decongestants (such as tetrahydrozoline hydrochloride or naphazoline), or a non-steroidal anti-inflammatory agent (such as nepafenac or ketorolac), corticosteroids (such as fluorometholone or loteprednol), or mast cell stabilizers (such as azelastie, cromal, emedastine, ketotifen, Iodoxamine, nedocromil, olopatadine, or pemirolast). If the dry eyes are associated with an infectious bacterial condition (such a meibomian gland infection or corneal infection) the eye drops are administered with or in a combination formulation can contain appropriate antibiotics (such as ciprofloxacin, erythromycin, gentamicin, ofloxacin, sulfacetamine, tobramycin, or monofloxacin). If the dry eyes are associated with a viral infection, the eye drops are administered with or in a combination formulation with an anti-viral agent such as trifluridine or idoxuridine.

Another example of a combination therapy is a subject who is diagnosed with both cutaneous lupus lesions on the face and/or ocular rosacea after presenting with irritated eyes and facial erythema with telangiectasia. The subject is treated with eye drops that contain the compound I, or a topical formulation that is applied to the face, and the subject is also treated with an oral antibiotic, such as a tetracycline antibiotic, such as minocycline. Alternatively the topical composition for treating the cutaneous LE, such as a gel for treating DLE, also contains a topical agent for treating rosacea, such as metronidazole gel.

In another example, the subject presents with cutaneous lupus and another pre-existing autoimmune disorder, and is treated with the topical formulation that contains compound I. The subject is also treated with systemic (for example) oral corticosteroid therapy, such as a tapering dose of prednisolone.

Example 9

Topical Applicators and Dosage Forms

Embodiments of the disclosed pharmaceutical compositions may be used in an application device that permits application of the composition to a target site on the skin without applying the composition to non-target site areas of the skin. For example, a device may be employed that allows the composition to be applied without first applying the composition to one's fingers. Suitable devices include spatulas, swabs, syringes without needles, and adhesive patches. Use of spatulas or swabs, or the like may require the device to be inserted into a container containing the composition. Using syringes or adhesive patches may be accomplished by filling the syringe or patch with the composition. The composition may then be topically spread by the spatulas or swabs, or may be expelled from the syringes onto the person's skin.

The topical formulation may be prepared in a variety of forms. Solids are generally firm and non-pourable and commonly are formulated as a bar or stick, or in particulate form; solids may be opaque or transparent, and optionally may contain solvents (including water and alcohol), emulsifiers, moisturizers, emollients, fragrances, dyes/colorants, preservatives and active ingredients. Creams and lotions are often similar to one another, differing mainly in their viscosity (creams are typically thicker and more viscous than lotions); both lotions and creams may be opaque, translucent or clear and often contain emulsifiers, solvents (including water and alcohol) and viscosity adjusting agents. Lotions and creams also may optionally contain moisturizers and emollients (especially in the case of skin care products), as well as fragrances, dyes/colorants, preservatives and active ingredients. Gels/serums may be prepared with a range of viscosities, from thick (high viscosity) to thin (low viscosity) and differ principally from lotions and creams in that gels/serums are usually clear rather than opaque. Like lotions and creams, gels/serums often contain emulsifiers, solvents (including water and alcohol) and viscosity adjusters, and may also contain moisturizers and emollients, fragrances, dyes/colorants, preservatives and active ingredients as described herein. Aqueous liquids are thinner than creams, lotions or gels, and are generally transparent; liquids usually do not contain emulsifiers. Liquid topical products often contain other solvents in addition to water (including alcohol) and may also contain viscosity adjusters, moisturizers and emollients, fragrances, dyes/colorants/pigments, preservatives and active ingredients.

Suitable secondary active ingredients for use in the formulations include, but are not limited to, alpha hydroxy acids, sunscreens, antiperspirants, anti-acne drugs, vitamins (especially vitamins A and C) and minerals, and various prescription and over-the-counter medications. The compositions disclosed herein can have multiple active ingredients within the same topical formulation, and combinations of active ingredients such as those listed above may be used, as appropriate for the condition or conditions being treated.

Other suitable additional and adjunct ingredients which may be included in the formulations include, but are not limited to, abrasives, absorbents, anti-caking agents, anti-foaming agents, anti-static agents, astringents (e.g., witch hazel, alcohol, and herbal extracts such as chamomile extract), binders (e.g., starch, cellulose ethers, microcrystalline cellulose, calcium hydrogen phosphate, calcium phosphate dibasic, and calcium sulfate dihydrate), excipients (e.g., polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose), buffering agents, chelating agents (e.g., Versene® EDTA), film forming agents, conditioning agents, opacifying agents (e.g., titanium dioxide), pH adjusters (e.g., citric acid and sodium hydroxide), and protectants. Examples of each of these ingredients, as well as examples of other suitable ingredients in topical product formulations, may be found in publications by The Cosmetic, Toiletry, and Fragrance Association (CTFA). See, e.g., CTFA Cosmetic Ingredient Handbook, 2nd edition, eds. John A. Wenninger and G. N. McEwen, Jr. (CTFA, 1992).

Other methodologies and materials for preparing formulations in a variety of forms are also described in Anthony L. L. Hunting (ed.), "A Formulary of Cosmetic Preparations (Vol. 2)—Creams, Lotions and Milks," Micelle Press (England, N.J. 1993). See, for example, Chapter 7, pp. 5-14 (oils and gels); Chapter 8, pp. 15-98 (bases and emulsions); Chapter 9, pp. 101-120 ("all-purpose products"); Chapter 10, pp. 121-184 (cleansing masks, creams, lotions); Chapter 11, pp. 185-208 (foundation, vanishing and day creams); Chapter 12, pp. 209-254 (emollients); Chapter 13, pp. 297-324 (facial treatment products); Chapter 14, pp. 325-380 (hand products); Chapter 15, pp. 381-460 (body and skin creams and lotions); and Chapter 16, pp. 461-484 (baby products); the contents of which are incorporated herein by reference.

Example 10

An Exemplary Topical Formulation

The topical formulation may be prepared in a variety of strengths and using a variety of excipient concentrations as described herein. Table 2, previously presented, provides a list of the excipients used in this example, and without being limited to any particular theory, the function of each excipient.

With reference to Table 2, PEG400 employed in working examples was Super Refined Polyethylene Glycol 400, commercially available from Croda Inc., Edison N.J. Likewise, Super Refined dimethyl isosorbide (DMI), also available from Croda Inc. typically was used in these examples.

To prepare the formulations, excipients and compound I were added to a glass container, and heated and/or sonicated at 65° C. to 70° C. to dissolve the API completely. The sample is then cooled to room temperature. The ingredients for two exemplary formulations prepared by this method are set forth below in Tables 12 and 13.

TABLE 12

| Component | Grade | Weight % | Weight (g) per kg |
|---|---|---|---|
| Compound I | GMP | 3.0 | 30 |
| Super Refined Polyethylene Glycol 400 | NF | 39.95 | 399.5 |

TABLE 12-continued

| Component | Grade | Weight % | Weight (g) per kg |
|---|---|---|---|
| Polyethylene Glycol 4500 | NF | 32.0 | 320 |
| Butylated Hydroxytoluene, Granular | NF | 1.0 | 10 |
| MYRJ S100-PA-SG | — | 5.0 | 50 |
| Super Refined Dimethyl Isosorbide | — | 15.0 | 150 |
| Purified Water | USP | 4.0 | 40 |
| Caramel | NF | 0.05 | 0.5 |
| | Total | 100 | 1000 |

TABLE 13

| Component | Grade | Weight % | Weight (g) per kg |
|---|---|---|---|
| Compound I | GMP | 6.0 | 60 |
| Super Refined Polyethylene Glycol 400 | NF | 33.95 | 339.5 |
| Polyethylene Glycol 4500 | NF | 35.0 | 350 |
| Butylated Hydroxytoluene, Granular | NF | 1.0 | 10 |
| MYRJ S100-PA-SG | — | 5.0 | 50 |
| Super Refined Dimethyl Isosorbide | — | 15.0 | 150 |
| Purified Water | USP | 4.0 | 40 |
| Caramel | NF | 0.05 | 0.5 |
| | Total | 100 | 1000 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A pharmaceutical ointment formulation for topical administration, comprising:

a therapeutically effective amount of from about 0.1% to about 10% (w/w) of compound I having a formula

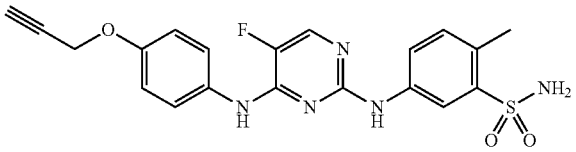

or a pharmaceutically acceptable salt thereof;

from 15% to 40% (w/w) of a topical base comprising polyethylene glycol having an average molecular weight of from about 3000 to about 8000 daltons;

from 0.5% to 1.5% (w/w) of an antioxidant;

from 3% to 15% (w/w) of an emollient;

from 10% to 20% (w/w) of a penetration enhancer;

from 25% to 50% (w/w) of a water-miscible solvent; *and* from 3% to 9% (w/w) of a surfactant[; and from 0.05% to 0.25% (w/w) of a colorant].

2. The pharmaceutical formulation of claim 1, comprising:

from 0.2% to 6% (w/w) of compound I or a pharmaceutically acceptable salt thereof;

from 30% to 40% (w/w) polyethylene glycol with an average molecular weight from 4000-5000 daltons;

from 30% to 40% (w/w) polyethylene glycol with an average molecular weight from 300 to 500 daltons;

15% (w/w) dimethyl isosorbide;

3% to 5% (w/w) water;

5% (w/w) polyethylene glycol monostearate; *and*

1% (w/w) butylated hydroxytoluene[; and from 0.05% to 0.25% (w/w) of the colorant].

3. The pharmaceutical formulation of claim 1, comprising 1% (w/w) compound I, from 25% to 40% (w/w) polyethylene glycol with an average molecular weight of 4500 daltons, and from 30% to 45% (w/w) polyethylene glycol with an average molecular weight of 400 daltons.

4. The pharmaceutical formulation of claim 1, comprising 3% (w/w) compound I, 32% (w/w) polyethylene glycol with an average molecular weight of 4500 daltons, and from 38% to 42% (w/w) polyethylene glycol with an average molecular weight of 400 daltons.

5. The pharmaceutical formulation of claim 1, comprising 6% (w/w) compound I, 35% (w/w) polyethylene glycol with an average molecular weight of 4500 daltons, and from 33% to 35% (w/w) polyethylene glycol with an average molecular weight of 400 daltons.

6. The pharmaceutical formulation of claim 1, comprising 1% (w/w) compound I, 20% (w/w) polyethylene glycol with an average molecular weight of 4500 daltons, and 48% (w/w) polyethylene glycol with an average molecular weight of 400 daltons.

7. The pharmaceutical formulation of claim 1, comprising 3% (w/w) compound I, 20% (w/w) polyethylene glycol with an average molecular weight of 4500 daltons, and 46% (w/w) polyethylene glycol with an average molecular weight of 400 daltons.

8. The pharmaceutical formulation of claim 1, comprising 6% (w/w) compound I, 20% (w/w) polyethylene glycol with an average molecular weight of 4500 daltons, and 43% (w/w) polyethylene glycol with an average molecular weight of 400 daltons.

9. The pharmaceutical formulation of claim 1, where the water-miscible solvent is a polyalkylene glycol with an average molecular weight from 200-600 daltons.

10. The pharmaceutical formulation according to claim 1 where the water-miscible solvent comprises PEG-400.

11. The pharmaceutical formulation according to claim 10 wherein the PEG-400 is substantially free of impurities.

12. The pharmaceutical formulation according to claim 11 wherein the PEG-400 comprises less than about 65 ppm formaldehyde.

13. The pharmaceutical formulation according to claim 11 wherein the PEG-400 comprises less than about 10 ppm formaldehyde.

14. The pharmaceutical formulation according to claim 11 wherein the PEG-400 comprises 1 ppm or less formaldehyde.

15. The pharmaceutical formulation of claim 1, where the penetration enhancer is dimethyl isosorbide, propylene glycol, or a combination thereof.

16. The pharmaceutical formulation of claim 1, where the emollient comprises water.

17. The pharmaceutical formulation of claim 1, where the surfactant is a sorbitan monostearate, a polyethylene glycol monostearate, D-α-tocopheryl polyethylene glycol 1000 succinate, a composition comprising glycol stearate/PEG32 stearate/PEG6 stearate, or a combination thereof.

18. The pharmaceutical formulation of claim 1, wherein the antioxidant is selected from the group consisting of butylated hydroxyanisole, butylated hydroxytoluene, ascorbic acid, a tocopherol and combinations thereof.

19. The pharmaceutical formulation of claim 18, where the antioxidant is butylated hydroxytoluene.

20. The pharmaceutical formulation of claim 1, [where the colorant is] *further comprising* 0.05-0.25% (w/w) [caramel] *colorant*.

21. The pharmaceutical formulation of claim 1, where the topical base comprises polyalkylene glycol having an average molecular weight from 4000-5000 daltons, the water-miscible solvent is a polyalkylene glycol having an average molecular weight of 300-500 daltons, the penetration enhancer is dimethyl isosorbide, the emollient is water, the surfactant is a polyethylene glycol monostearate, *and* the antioxidant is butylated hydroxytoluene[, and the colorant is caramel colorant].

22. The pharmaceutical formulation of claim 1, further comprising a fragrance, an absorbent, an astringent, a binder, a buffering agent, a chelating agent, a film-forming agent, a conditioning agent, an opacifying agent, a protectant, *a colorant,* or any combination thereof.

23. A pharmaceutical ointment formulation, comprising:

3% (w/w) of compound I or a pharmaceutically acceptable salt thereof;

32% (w/w) polyethylene glycol 4500;

39.95% (w/w) polyethylene glycol 400;

15% (w/w) dimethyl isosorbide;

4% (w/w) water;

5% (w/w) polyoxyl stearate 100; *and*

1% (w/w) butylated hydroxytoluene[; and 0.05% caramel colorant].

24. A pharmaceutical ointment formulation, comprising:

6% (w/w) of compound I or a pharmaceutically acceptable salt thereof;

35% (w/w) polyethylene glycol 4500;

33.95% (w/w) polyethylene glycol 400;

15% (w/w) dimethyl isosorbide;

4% (w/w) water;

5% (w/w) polyoxyl stearate 100; *and*

1% (w/w) butylated hydroxytoluene[; and 0.05% caramel colorant].

25. A method of treating cutaneous lupus, comprising topically administering to a subject a pharmaceutical ointment formulation comprising:

from 0.1% to 10% (w/w) of a compound I having a formula

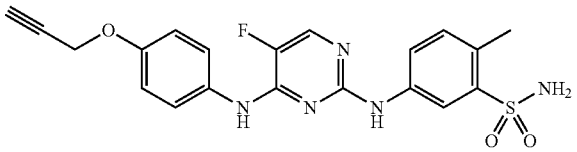

or a pharmaceutically effective salt thereof;

from 15% to 40% (w/w) of a topical base comprising polyethylene glycol having an average molecular weight of from about 3000 to about 8000 daltons;

from 25% to 50% (w/w) of a water-miscible solvent;

from 10% to 20% (w/w) of a penetration enhancer;

from 3% to 15% (w/w) of an emollient;

from 3% to 9% (w/w) of a surfactant; *and* from 0.5% to 1.5% (w/w) of an antioxidant[; and from 0.05% to 0.25% (w/w) of a colorant].

26. The method of claim 25, comprising:

from 0.2% to 6% (w/w) of compound I or a pharmaceutically acceptable salt thereof;

from 30% to 40% (w/w) polyethylene glycol with an average molecular weight from 4000-5000 daltons;

from 30% to 40% (w/w) polyethylene glycol with an average molecular weight from 300-500 daltons;

15% (w/w) dimethyl isosorbide;

3% to 5% (w/w) water;

5% (w/w) polyethylene glycol monostearate; and

1% (w/w) butylated hydroxytoluene.

27. The method of claim 26, where the pharmaceutical formulation comprises 1% (w/w) compound I, 25% to 40% (w/w) polyethylene glycol with an average molecular weight of 4500 daltons, and 30% to 45% (w/w) polyethylene glycol with an average molecular weight of 400 daltons.

28. The method of claim 25, where the subject has cutaneous lupus lesions, and the pharmaceutical formulation is applied topically to the cutaneous lupus lesions.

*29. The pharmaceutical ointment formulation of claim 23 further comprising a colorant.*

*30. The pharmaceutical ointment formulation of claim 24 further comprising a colorant.*

*31. The method of claim 25 wherein the pharmaceutical formulation further comprises a colorant.*

*32. The method of claim 31 wherein the colorant is caramel.*

* * * * *